United States Patent
Williams

(10) Patent No.: US 12,133,486 B2
(45) Date of Patent: *Nov. 5, 2024

(54) METHODS OF PROPAGATION OF ARBUSCULAR MYCORRHIZAL FUNGI (AMF) AND USES THEREOF

(71) Applicant: Terra Microbes, LLC, Laramie, WY (US)

(72) Inventor: Stephen Earl Williams, Laramie, WY (US)

(73) Assignee: Terra Microbes, LLC, Laramie, WY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/369,797

(22) Filed: Sep. 18, 2023

(65) Prior Publication Data

US 2024/0000025 A1    Jan. 4, 2024

Related U.S. Application Data

(63) Continuation of application No. 17/691,039, filed on Mar. 9, 2022, now Pat. No. 11,758,854.

(Continued)

(51) Int. Cl.
| | | |
|---|---|---|
| *A01G 18/10* | (2018.01) | |
| *A01G 11/00* | (2006.01) | |
| *A01G 18/20* | (2018.01) | |

(52) U.S. Cl.
CPC ............. *A01G 18/10* (2018.02); *A01G 11/00* (2013.01); *A01G 18/20* (2018.02)

(58) Field of Classification Search
CPC ........ A01G 11/00; A01G 18/10; A01G 18/20; A01G 24/20

(Continued)

(56) References Cited

U.S. PATENT DOCUMENTS

| | | |
|---|---|---|
| 6,759,232 B2 | 7/2004 | Wang |
| 7,036,273 B2 * | 5/2006 | Valiquette ................ A01G 7/06 47/64 |

(Continued)

FOREIGN PATENT DOCUMENTS

| | | |
|---|---|---|
| EP | 3038456 B1 | 3/2018 |
| WO | 91/01082 A1 | 2/1991 |

(Continued)

OTHER PUBLICATIONS

Jim Deacon, "Fungal spores, spore dormancy, and spore dispersal." Fungal biology (2005): 184-212.

(Continued)

*Primary Examiner* — David J Parsley
(74) *Attorney, Agent, or Firm* — Hathaway & Kunz, LLP; Thomas J. Siepmann

(57) ABSTRACT

Methods of propagating Arbuscular Mycorrhizal Fungi (AMF) are described that do not require the addition of, or presence of, any detectable live host plant material or live plant root material. The method comprises addition of water and optionally exposure to sunlight. It was surprisingly found that soil devoid of any detectable live host plant material, including host plant roots, is capable of supporting AMF reproduction, though it is widely believed that AMF are obligate symbionts requiring live plant roots for colonization to reproduce. Described methods optionally include active removal of living host plant material from the soil prior to AMF inoculation. Optionally, phosphorous compounds are added to the soil prior to inoculation. It was found that addition of phosphorous compounds, such as phosphite, to the soil enhances the growth of AMF spores by as much as three-fold over controls having no added phosphorous compounds.

16 Claims, 2 Drawing Sheets

Related U.S. Application Data

Figure 1:
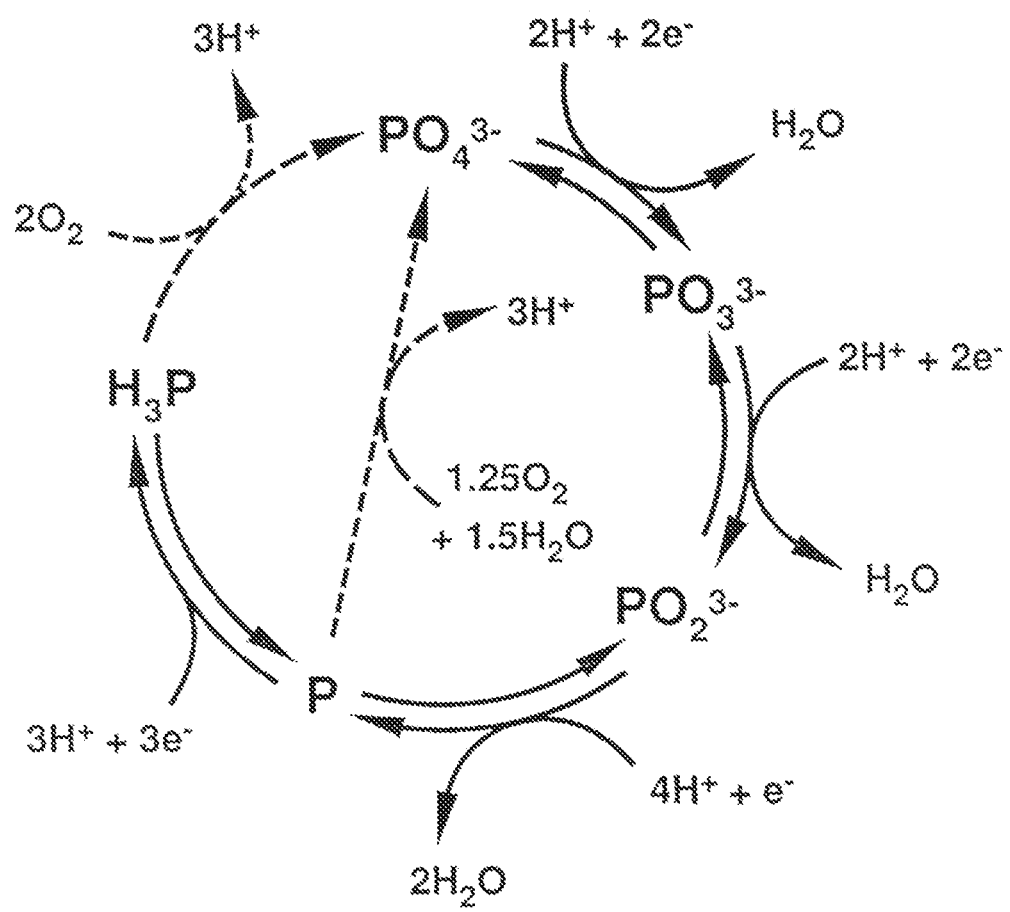

(60) Provisional application No. 63/275,886, filed on Nov. 4, 2021.

(58) Field of Classification Search
USPC .............................. 47/1.1, 58.1 R, 58.1 SC
See application file for complete search history.

(56) References Cited

U.S. PATENT DOCUMENTS

| | | | |
|---|---|---|---|
| 9,017,442 | B2 | 4/2015 | Johnson |
| 9,131,685 | B2 | 9/2015 | Dahmen et al. |
| 9,554,575 | B2 | 1/2017 | Smith et al. |
| 9,700,057 | B2 | 7/2017 | Kang et al. |
| 2009/0272029 | A1 | 11/2009 | Aiking et al. |
| 2014/0069008 | A1* | 3/2014 | Herrera-Estrella .... A01N 59/26 |
| | | | 47/59 R |
| 2015/0040629 | A1 | 2/2015 | Alok |
| 2015/0237807 | A1 | 8/2015 | Valiquette |
| 2016/0278296 | A1 | 9/2016 | Schuessler |
| 2019/0210935 | A1 | 7/2019 | Belcher et al. |
| 2019/0216025 | A1 | 7/2019 | Farmer et al. |
| 2019/0256431 | A1 | 8/2019 | Zaseybida et al. |
| 2020/0408731 | A1 | 12/2020 | Bai et al. |
| 2021/0032975 | A1 | 2/2021 | Teotonio Da Silva |

FOREIGN PATENT DOCUMENTS

| | | |
|---|---|---|
| WO | 2018/236227 A1 | 12/2018 |
| WO | 2019/018845 A1 | 1/2019 |

OTHER PUBLICATIONS

Gopal Selvakumar et al., "Arbuscular mycorrhizal fungi spore propagation using single spore as starter inoculum and a plant host." Journal of applied microbiology 124.6 (2018): 1556-1565.

Stanley E. Bellgard et al., "Response of mycorrhizal diversity to current climatic changes." Diversity 3.1 (2011): 8-90.

Miguel Montes-Borrego et al., "Arbuscular micorrhizal fungi associated with the olive crop across the Andalusian landscape: factors driving community differentiation." PLoS One 9.5 (2014): e96397.

Kai Wu et al., "Dissolved organic carbon in the South China Sea and its exchange with the Western Pacific Ocean." Deep Sea Research Part II: Topical Studies in Oceanography 122 (2015): 41-51.

Stanley W. Buol, et al. Soil genesis and classification. John Wiley & Sons, 2011, 1-30.

Leonie H. Luginbuehl et al., "Understanding the Arbuscule at the heart of Endomycorrhizal symbioses in plants." Current Biology 27.17 (2017): R952-R963.

Peter Oviatt et al., "Mycorrhizal technologies for an agriculture of the middle." Plants, People, Planet 3.5 (2021): 454-461.

Sigrun Dahlin, "Arbuscular Mycorrhizal Fungal (AMF) Inoculum Production Training-Report." (2018): 1-29.

Yue Hui et al., "Research Advances in Preparation of Arbuscular Mycorrhizal Fungi Inoculants." Plant Diseases & Pests 7.2 (2016): 26-30.

Arthur Schüssler et al., "The Glomeromycota: a species list with new families and new genera." (2010).1-60.

Martin R.Carter et al., Soil sampling and methods of analysis. CRC press, 2007, 1-1261.

Hoang Thi Bich Thao et al., "Phosphite (phosphorous acid): fungicide, fertilizer or bio-stimulator?." Soil science and plant nutrition 55.2 (2009): 228-234.

Ray Gavlak et al., "Soil, plant and water reference methods for the western region." WCC-103 Publication, Fort Collins, CO (2003), 1-207.

Ann Winne Rodman et al., Soils of Yellowstone National Park. Yellowstone Center for Resources, National Park Service, 1996, 1-333.

Anthony O. Adesemoye et al., "Plant-microbes interactions in enhanced fertilizer-use efficiency." Applied microbiology and biotechnology 85.1 (2009): 1-12.

PCT International Search Report and Written Opinion dated May 23, 2022, PCT International Application No. PCT/US22/19629, pp. 1-14.

Birgitte Neergaard Bearden, "Influence of arbuscular mycorrhizal fungi on soil structure and soil water characteristics of vertisols," Plant and Soil, 2001, vol. 229, pp. 245-258.

Nani G. Bhowmik et al., "Kankakee River Basin in Illinois: Hydraulics, Hydrology, River Geometry, and Sand Bars," Illinois State Water Survey, Feb. 2000, pp. 1-131.

\* cited by examiner

METHODS OF PROPAGATION OF ARBUSCULAR MYCORRHIZAL FUNGI (AMF) AND USES THEREOF

CROSS-REFERENCE TO RELATED APPLICATIONS

This application claims priority to U.S. patent application Ser. No. 17/691,039 filed on Mar. 17, 2022, issued as U.S. Pat. No. 11,758,854, which claims priority to U.S. Provisional Patent Application No. 63/275,886, filed Nov. 4, 2021, and is related to International Patent Application PCT/US2022/019629, filed on Mar. 9, 2022, the contents of all of which are incorporated by reference in their entirety for all purposes.

BACKGROUND

Mycorrhizal associations have been shown as critical for most land plants to acquire essential soil nutrients. In these associations, a harmony is established between plant and fungus where the fungus acquires fixed carbon from the plant and the plant receives nutrients derived from soil by the fungus. (Bellgard S. E and Williams S. E., *Diversity,* 3:8-2011).

Of several types of mycorrhizal associations, the arbuscular mycorrhizal fungi (AMF) have been the focus of much study. These fungi penetrate the plant root and root cells. Fungal structures that form inside root cells (arbuscules) are sites of nutrient exchange between fungus and plant. (See, Luginbuehl L. H and Oldroyd F. E. D., *Curr. Biol.,* 27:R952-R963, 2017).

AMF infect many Gymnosperms and most Angiosperms, including plants in native and crop systems. The scientific literature is rife with studies showing the positive impacts of these fungi on plants in general. (Jana, B.. "Mycorrhiza: A potential bio-enhancer in the agriculture production system," In: "Sangeetha, Beneficial Microbes for Sustainable Agriculture and Environmental Management," Apple Academic Press, Boca Raton, FL, 2020).

However, AMF have never been cultured on artificial media or in the absence of plants. The preponderance of failed attempts leads to the consensus that these fungi cannot be grown in the absence of host plants. Cultures are maintained where containerized soil is inoculated with AMF spores and host plants are seeded and grown. This culture process has become standard procedure to culture AMF.

Production of AMF in the absence of host plants is an impediment to their general use in agriculture, forestry, and reclamation. (Kahliq A. D, Bagyaraj J., and Alam M., "Advances in Mass Production Technology of Arbuscular Mycorrhiza," In: "Mycorrhizal Biotechnology," CRC Press, 2017, Thangadurai A. Ed.). Attempts to resolve this have focused on fungal carbon nutrition, basically examining use of plant derived compounds as growth media. Described herein are methods that resolves this impediment. The approach to this problem described herein is different from other attempts and contrary to established assumptions undergirding the canon of AMF research.

The first assumption in the AMF field is that phosphorus in biological systems and in the soil that feeds those systems exists only as highly oxidized phosphate ($PO_4^{3-}$). That is, it is assumed that phosphorous in such systems does not exist as more reduced forms such as phosphite ($PO_3^{3-}$), hypophosphite ($PO_2^{3-}$), elemental phosphorus ($P_0$), or even phosphide ($P^{3-}$, or when protonated, $H_3P$, also referred to as phosphine). The contention in the literature is that phosphorus in ecosystems, and specifically soils, does exist in various oxidation states but levels are low. There are published observations and experiments to support this. A phosphorus cycle based on oxidation/reduction is envisioned (see FIG. 1). The possibility that phosphorous is cycled has generally been ignored by researchers in the AMF field. There are reasons for this. Burford and Bremner examined the possibility of phosphate reduction to phosphine and concluded that such a conversion was unlikely to occur in soil. (See, Burford, J. R., and Bremner, J. M., *Soil Biol. Biochem.,* 4:489-495, 1972). As a result, examination of soils for transformation of phosphorus has been widely studied as only cycling of phosphate, see, e.g., Cole et al., *Microb. Ecol.,* 4:381-387, 1978, and as described in Devai et al., *Nature,* 333:343-345, 1988; however, phosphine was detected as being released from anaerobic treatment of sewage. Devai et al. also showed phosphine release by bacterial reduction of phosphate under laboratory conditions. The evidence of phosphate reduction to phosphine has gained enough traction that some textbooks make modest mention of this phenomenon. (See, Coyne M., "Soil Microbiology," Delmar Publishers, 1999, p. 198).

The second of these assumptions in the AMF field is that AMF cannot be generated in the absence of plants. However, described herein are observations that contradict this assumption. These observations made in soils of arid rangelands and grasslands, information in the literature, and several experiments together show that AMF are able to be generated in the absence of living plants or live plant material. The experiments described herein were conducted under the premise that the AMF need a carbon source, but also that they also need an energy source separate from the carbon source.

This concept also thwarts a basic biological assumption that only prokaryotic organisms (bacteria and archae) have the capacity to split their carbon and energy sources. Further, eukaryotic organisms, like fungi and higher organisms, cannot split their carbon and energy sources. AMF are considered eukaryotic organisms, but recent information has changed the position of these fungi on the evolutionary scale. Up until recently the taxonomy of AMF placed them in the Phycomycetes, a fungal classification equivalent to other fungi. Based on new genetic evidence, AMF have been reclassified into a new taxon, the Glomeromycetes, a subphylum. Further, genetic evidence suggests the AMF are the progenitors of all fungal-like organisms that accompanied plants from the oceans to land and are among the very earliest of fungi. (See, Luginbuehl L. H. and Oldroyd).

SUMMARY

Provided are methods of propagating arbuscular mycorrhizae fungi. The described methods include various steps. The various steps include, for example, the following: providing an active culture of arbuscular mycorrhizae fungi (AMF) spores, providing soil comprising phosphorous and organic carbon, inoculating the soil with the active culture of AMF, optionally exposing the soil to light; and adding water to the soil. In some embodiments, no live plant material of any kind is added to the soil prior to or after inoculation of the soil with the live AMF culture, e.g., not added at any point during the method, and the AMF are able to grow despite the lack of live plant material. In some embodiments, the provided soil comprises little or no live plant material or an amount of live plant material that is lower than the limit of detection. In other embodiments, the amount of live plant material present in the soil is at a level that is below detection limits, i.e., is undetectable. In other embodiments, the AMF do not form detectable appressoria with any live plant root host during propagation, and there is no detectable symbiosis of AMF with host plant material during propagation. In such embodiments, after addition of water, the AMF spores germinate and reproduce despite the fact that there is no detectable amount of live plant material in the soil. In various embodiments of the methods described herein, the method further comprises actively removing living plant material from the soil by such means as contacting the soil with steam, optionally pressurized steam, UV radiation, and/or ethylene oxide. This contacting step is performed, in such embodiments, until the level of living plant material in the soil is undetectable. In such embodiments, removing living plant material from the soil comprises removing AMF symbiotic plant material such that AMF symbiotic plant material is not detectable in the soil.

In some embodiments of the described methods, the arbuscular mycorrhizae do not comprise ectomycorrhizae, ericoid mycorrhizae, orchid mycorrhizae, arbutoid mycorrhizae, ectendo mycorrhizae, or monotropoid mycorrhizae. In various embodiments of the described methods, the AMF culture comprises mycorrhizae mycobionts that form arbuscules with symbiotic plants. In other embodiments, the AMF culture of the described methods comprises one or more *mycorrhiza* species from genera including *Paraglomus, Archaeospora, Geosiphon, Ambispora, Sclerocystis, Rhizophagus, Septoglomus, Funneliformis, Glomus, Claroideoglomus, Racocetra, Cetraspora, Dentiscutata, Gigaspora, Scutellospora, Pacispora, Acaulspora,* and *Redeckera,* and/or one or more *mycorrhiza* species from families including Paraglomeraceae, Archaeosporaceae, Geosiphonaceae, Ambisporaceae, Glomoeraceae, Claroideoglomeraceae, Gigasporaceae, Pacisporaceae, Acaulosporaceae, and Diversisporaceae, and/or one or more *mycorrhiza* species including at least *Claroideoglomus etunicatum* (*Glomus etunicatum*), *Rhizophagus clarus* (*Glomus clarum*), *Rhizophagus intraradices* (*Glomus intraradices*), and *Septoglomus deserticola* (*Glomus deserticola*). (See, Redecker et al., "An evidence based consensus for the classification of arbuscular mycorrhizal fungi (Glomeromycota)," *Mycorrhiza*, 23:515-531, 2013).

In some embodiments of the described methods, the soil is supplemented with sand at 50 to 75 wt %, such as, for instance, fine silica sand #4 or quartz sand of 0.05 mm to 2 mm diameter.

The soil in the described methods, in some embodiments, has a pH of between about 5.3 and about 8.5, or a pH of about 7.3 to about 7.9. In various described embodiments of these methods, the soil comprises a total organic carbon (TOC) content of greater than 0.5 wt % and less than 4.0 wt %. In such embodiments, the organic matter is free of living plant material, or free from detectable quantities of living plant material. In such embodiments, the organic matter is determined by various means, such as, for instance, by dry combustion or by dichromate redox. In such embodiments, the organic matter comprises dead and decaying remains of plants, animals, microorganisms, and associated metabolic waste thereof. In certain embodiments, the soil is air-dried prior to inoculation and after steaming.

In various embodiments of the described methods, the soil is one or more soil types selected from Entisols, Aridisols, Inceptisols, Alfisols, Spodosols, Ultisols, Oxisols, Mollisols, Vertisols, Histosols, Gelisols, and Andisols. In a specific embodiment, the soil is a Morset series soil or Lymanson series soil. In other embodiments, the soil is a fine-loamy mixed Argic Cryoboroll.

Some embodiments of the described methods further comprise the additional step of sifting the soil through a sieve comprising openings or holes of about 4 mm in diameter prior to inoculating the soil to remove large particulates from the soil. In other embodiments described herein, the methods also include other steps such as, for instance, first adding an initial amount of water upon inoculation, and then adding water every third day after inoculating, as the step in which water is added. In other embodiments, adding water to the soil comprises: a) adding an initial 400 mL water per 3,055 g of soil, and then b) 100 mL per 3,055 g of soil every third day.

In various additional embodiments of the described methods, the phosphorous is: (a) phosphate anion $PO_4^{3-}$ and/or phosphite anion $PO_3^{3-}$, and/or (b) as potassium salts $K_2HPO_4$ and/or $K_2HPO_3$.

Various embodiments of the described methods also include the optional step of exposing the inoculated soil to light. In such embodiments where the soil is exposed to light, the light is in some instances full spectrum luminous flux. In other embodiments, the light is at least 24,000 lumens. In some embodiments, the lighting step is performed for a period of about 8 to about 20 hours during a 24 hour period, for instance.

In the inoculation step of the methods described herein, the amount of AMF spores in the soil after inoculation is about 2 to 10 spores per gram of soil. In some embodiments, a sufficient amount of active culture of AMF is added to the soil such that the final density of spores in the inoculated soil is at least 4 spores per gram of inoculated soil.

This Summary is provided to introduce a selection of concepts in streamlined forms that are further described below in the Detailed Description. This Summary is not intended to identify critical or essential features of the claimed subject matter, nor is it intended to fully limit the scope of the claimed subject matter described more fully hereinbelow.

BRIEF DESCRIPTION OF THE DRAWINGS/FIGURES

For a more precise understanding of the disclosed methods and compositions, reference is made to specific embodiments thereof illustrated in the drawings. The drawings presented herein are not drawn to scale and any reference to dimensions in the drawings or the following description are with reference to specific embodiments. It will be clear to one of skill in the art that variations of these methods are possible while still maintaining full functionality for the intended purpose. Such variations are specifically contemplated and incorporated into this disclosure notwithstanding the specific embodiments set forth in the following drawings.

FIG. 1. A proposed phosphorus cycle. Phosphate ($PO_4^{-3}$) is reduced to phosphite ($PO_3^{-3}$) and hypophosphite ($PO_2^{-3}$) and then elemental P. Further reduction is possible to phosphine ($H_3P$), a gas. On exposure to oxygen, phosphine ($H_3P$) can be oxidized chemically to phosphate ($PO_4^{-3}$). However, evidence suggests that phosphine ($H_3P$) can be sequentially oxidized back to P and then on to hypophosphite ($PO_2^{-3}$), phosphite ($PO_3^{-3}$) and then to phosphate ($PO_4^{-3}$). The step phosphite ($PO_3^{-3}$) to phosphate ($PO_4^{-3}$) is well documented as biological.

Figure 2:
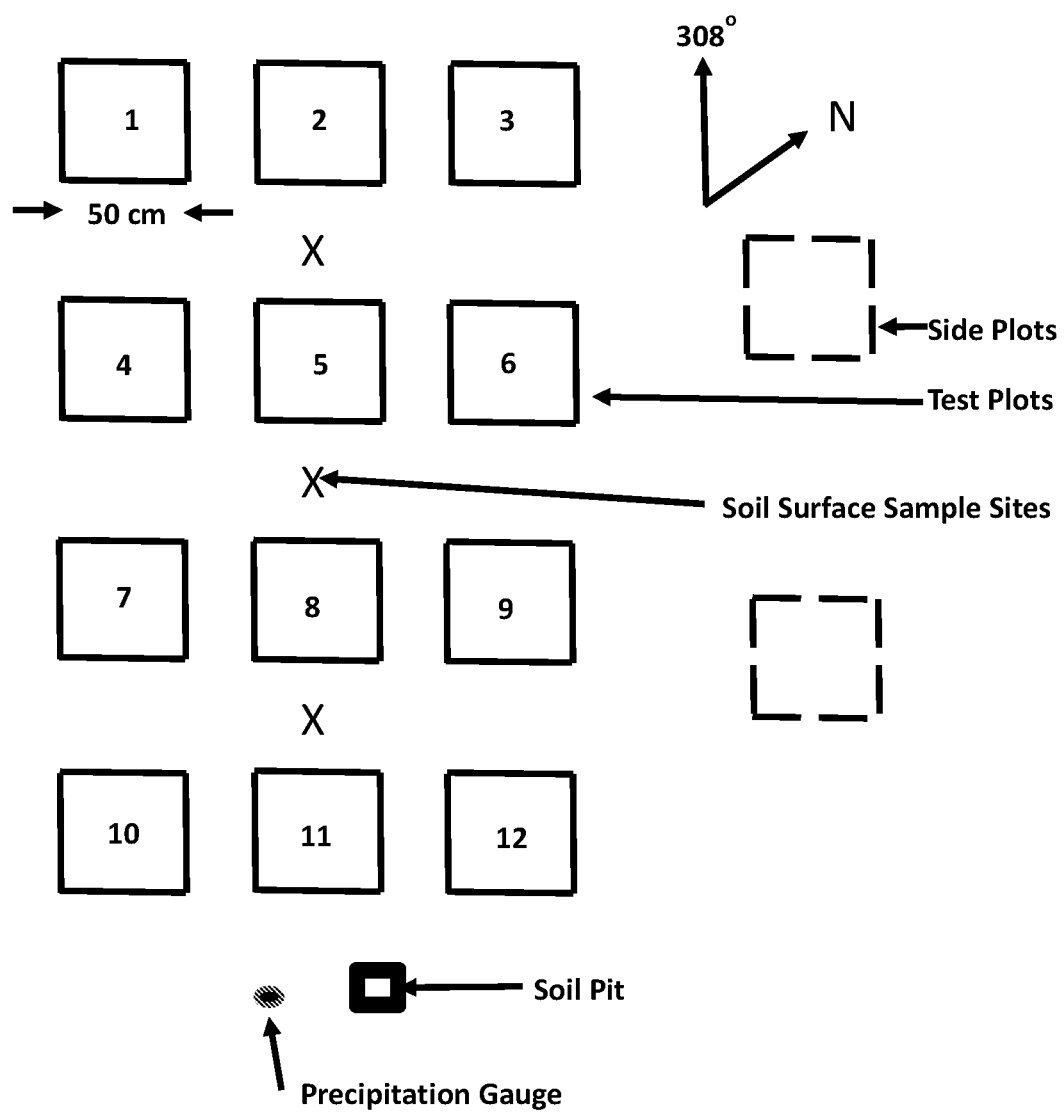

FIG. 2 provides a surface view of a field study site, Lat./Long.: 41.32 N and 105.67 W, elevation 2,277 M. Plot treatments include: controls (plots 1, 6, and 8), KCl plots (plots 2, 4, and 12), phosphate plots (plots 3, 7, and 11), and phosphite plots (plots 5, 9, and 10).

DETAILED DESCRIPTION

Definitions

The term "a" or "an" entity as used herein refers to one or more of that entity; for example, "an additive," is understood to represent one or more additives. As such, the terms "a" (or "an"), "one or more," and "at least one" are used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Ranges provided herein are understood to be shorthand for all of the values within the stated range. For example, a range of 1 to 20 is understood to include any number, combination of numbers, or sub-range, from the group consisting 1, 2, 3, 4, 5, 6, 7, 8, 9, 10, 11, 12, 13, 14, 15, 16, 17, 18, 19, and 20, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

The transitional term "comprising," which is synonymous with "including," or "containing," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed methods described herein.

Unless specifically stated or obvious from context provided herein, as used herein, the term "or" is understood to be inclusive. Unless specifically stated or obvious from context, as used herein, the terms "a," "an," and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. That is, as used herein, in some instances the term "about" or "approximately" refers to a variation of 10% from the indicated values (e.g., 50%, 45%, 40%, etc.), or in case of a range of values, means a 10% variation from both the lower and upper limits of such ranges. For instance, "about 50%" refers to a range of between 45% and 55%.

Units, prefixes, and symbols are denoted in their Systeme International de Unites (SI) accepted form. Numeric ranges are inclusive of the numbers defining the range. The headings provided herein are not limitations of the various aspects or aspects of the disclosure, which can be had by reference to the specification as a whole. Accordingly, the terms defined immediately below are more fully defined by reference to the specification in its entirety.

The terms obligate mycorrhizal or mycotrophic, as used herein, means a plant that is highly dependent on AM fungi associations in order to reach reproductive maturity.

The terms facultative mycorrhizal or mycotrophic as used herein means a plant that is capable of taking advantage of AM fungal associations, but also can achieve in some instances reproductive maturity without AM fungal association.

The terms non-mycorrhizal or non-mycotrophic, as used herein, mean a plant that is capable of reaching reproductive maturity without AM fungal associations.

Oxidation/Reduction (or redox), as used herein, means a process of adding or removing electrons to chemical compounds or single atomic species such that they undergo oxidization or reduction, depending on whether the electron is added or removed from the chemical species. When a species is reduced, its oxidation number, or in the case of a single element, its valence, is decreased. Oxidation is numerically the opposite, that is the oxidation number or valence is increased.

Phosphorus is an inorganic compound. (See, Corbridge, 2013, CRC Press, Boca Raton, FL). Phosphorus exists at every valence (or oxidation state) from +5 to −3. The +4, +1, −1, and −2 are not always shown herein. Elemental phosphorus is represented by the letter P, herein and is occasionally written as P4 (white phosphorus). Elemental P exists as several color variants, including white, violet, black, red, and others, each of which have different structures. White P is tetrahedral. White phosphorus spontaneously ignites and is dangerously reactive in air. It is very toxic by inhalation or digestion. The valence of P is 0 (zero).

Phosphoric acid is also written as $H_3PO_4$. Among the various salts of phosphoric acid are the potassium salts: $KH_2PO_4$, $K_2HPO_4$ or $K_3PO_4$, also referred to herein as monopotassium phosphate, dipotassium phosphate, and tripotassium phosphate, respectfully. Most phosphorus on earth exists as the phosphate anion and in numerous insoluble complexes. The valence of phosphate phosphorus is +5.

Phosphorous acid (phosphonic acid) is also written herein as $H_3PO_3$. Exemplary potassium salts of phosphorous acid are $KH_2PO_3$ and $K_2HPO_3$, also called monopotassium phosphite and dipotassium phosphite, respectively.

Phosphites are uncommon in the environment, but at times exist under anoxic conditions. The acid and presumably the salts of phosphites exist in tautomeric forms. The valence of phosphite is +3.

Hypophosphorous acid is also referred to herein as phosphinic acid and as $H_3PO_2$. An exemplary potassium salt of phosphinic acid is monopotassium hypophosphite or $KH_2PO_2$. The valence of hypophosphite phosphorus is +1.

White phosphorous is elemental phosphorous (P), and is also sometimes referred to as yellow phosphorous, and appears as a white to yellow transparent waxy crystalline solid that turns a darker color when exposed to light. White phosphorous is self-igniting, highly toxic, and used in industry to manufacture fertilizers, food additives, cleaning compounds, and weapons.

Phosphine, $PH_3$ (sometimes written herein as $H_3P$) is a colorless gas that is spontaneous flammable in air. Phosphine is extremely toxic, but is generated biologically under highly anoxic conditions. Phosphine reacts with metals to form metal phosphides, e.g., tripotassium phosphide, or $K_3P$.

Phosphine has a valence of −3. Certain environmental parameters are required for the generation of phosphine ($PH_3$), such as specific temperatures, presence of organic matter, and moisture. However, a reducing environment (low Eh, redox potential) is essential to producing phosphine. Redox potential is the tendency of electrons to flow between compounds. The redox potential required for the reduction of phosphate to phosphine is about −345 mV at pH of 7.0. (See, Coyne, Mark S., 1999, "Introduction to Soil Microbiology," Delmar Cengage Learning, Delmar Publishers, Albany, NY). Further, this reaction is energetically difficult. The reduction is estimated to require about 1100 kcal per mole. As stated in White and Medcalf, "[n]evertheless, production of reduced P compounds has been documented and thus nature has obviously found a way to circumvent this difficulty." (See, White and Medcalf, 2007, *Annu. Rev. Microbiol.*, 61:379-400). Historical records of the production of phosphine gas identified the "Will-O-the-Wisp," as a greenish glow of bogs on dark, summer nights as the oxidation of this gas diffused from the organic milieu. Early accounts, although anecdotal, have been confirmed. (Devai et al., *Nature,* 333:343-345; White and Medcalf, 2007, *Ibid.*).

The term symbiosis, as used herein, is meant to indicate the usually obligatory cohabitation of two dissimilar organisms in intimate association. Often, but not always, this cohabitation is mutually beneficial. (See, Coyne, Mark S., 1999, "Introduction to Soil Microbiology," Delmar Publishers). Symbiosis also means a close, temporary (non-hereditary), or lasting (hereditary), association between two organisms of different species, one being considered as the symbiont and the other as the host, living closely together, sometimes in mutually beneficial manner. The host provides a nutritional environment to the endosymbiont. Without being limiting, this also includes cell organelles resulting from previous endosymbiotic events, as well as organelles created artificially, and modified prokaryotes or eukaryotes designed to function inside living cells as artificial organelles.

The term "chemolithotroph" and alternately referred to as chemoautotroph, as used herein means an organism that catabolizes $CO_2$ or carbonates as its sole source of carbon for cell biosynthesis and that generates energy from the oxidation of reduced inorganic compounds.

The term "chemoorganotroph" or alternately referred to herein as heterotroph, as used herein means an organism for which organic compounds serve as both energy and carbon sources for cell synthesis.

The term "photolithotroph" as used herein means an organism that uses light as a source of energy and uses $CO_2$ or carbonates as the source of carbon for cell biosynthesis.

A "saprophyte," as that term is used herein, is an organism that survives utilizing dead or decaying organic material as its energy source.

The term "vesicle," as used herein is a structure of many, but not all, of the AM fungi that is often inside the plant host root but may also optionally be outside of the root in the soil. Vesicles function as storage structures, often having microscopically visible droplets of oil in them.

An "active culture" as the phrase is used herein means a biomass of live cells actively growing or capable of growing in a culture medium (substrate) contained in a suitable vessel. Exemplary suitable vessels include, for instance, a container open to the atmosphere and often described in literature within the field simply as a pot. The active culture comprises at least one live fungus that is reproduction competent.

The term "plant material" as used herein means living plant tissue and cells produced by a photosynthetic process. Plant material includes all living plant tissues including parts of plants growing below the surface, such as, but not limited to, roots, root hairs, root caps, meristems, as well as parts of plants growing above the surface, such as, but not limited to, shoots, buds, leaves, nodes, stems, petioles, flowers, seeds, and components or parts or cells thereof.

As used herein, the term "sand" means a soil mineral fraction whose particles have a diameter of between 2 mm and 0.05 mm, and composed mostly of oxidized silicon materials having metamorphic origins or carbonate materials (usually calcium or magnesium) having sedimentary origins. Sands do not include silts (0.05 mm to 0.002 mm diameter) or clays (0.002 mm and smaller diameter). (See, Plaster, E. J., "Soil Science and Management," Delmar Publishers, 1997, ISBN 08-273-72930). Sand is either synthetic or naturally-sourced or a combination thereof.

The phrase "total organic carbon," or alternately referred to herein as "organic carbon" or "organic matter" is the amount of carbon found in an organic compound and is often determined by dry combustion or by dichromate redox, and comprises dead and decaying remains of plants, animals, microorganisms, and associated metabolic waste thereof. Other methods of measurement are known, such as acidification, oxidation, combustion, high temperature catalytic oxidation, photo-oxidation, ultraviolet/persulfate oxidation, conductivity, non-dispersive infrared, and the like. Generally, TOC in a sample is indicative of carbon atoms bound covalently in organic compounds. Examples of organic matter are plant or animal based, or synthetic substances containing carbon and other elements defining organic compounds. Generally, as used herein, organic carbon and/or organic matter does not include living matter, i.e., living plant material, plant cells, or plant parts. TOC and organic carbon do not include inorganic compounds comprising carbon, such as carbonates. A measurement of TOC does not provide information about which specific organic carbon compounds are in the sample, but instead provides a quantitation of the amount of organic compound in total in a sample in general of any type, combined into one numerical value or estimated value.

The term "spore" as used herein means microscopic biological particles that, in this case, allow fungi to reproduce, similar to a seed in most green, vascular plants. Spores of AMF can vary in size down to as small as 2 microns in diameter, depending on the species. Spores are produced by living fungi, as a result of sexual or asexual reproduction, as a means of reproduction. Spores of AMF are generally borne in the soil and can be airborne during wind erosion of soil. Spores are in some cases haploid and can grow into mature haploid individuals through mitotic division of cells. In fungi, spores are often classified by the structure in which meiosis and spore production occurs, or by function, origin during life cycle, or based on mobility.

As used herein, the term "propagation" means multiplication, growth, germination, reproduction, or otherwise increasing the number or quantity of AMF. Propagation is to be understood as also encompassing micropropagation methods, such as those in aseptic tissue culture and the like. Micropropagation is understood to mean propagation from AMF spores in laboratory settings in sterile or nearly sterile conditions. Propagation is meant to encompass the growth of AMF in any and all conditions including in soil and/or soilless medium as described by the methods disclosed herein. Propagation may also refer, in certain contexts herein, to the addition of AMF live cultures obtained by the methods described herein to a crop or other plant for the purpose of propagating or growing that crop or other plants.

Any compositions or methods provided herein are contemplated as combinable with one or more of any of the other compositions and methods provided herein. Likewise, method steps, while in some instances presented in a specific order or described in a certain order in the following description, differently ordered steps are also contemplated. Thus, the order of steps, and number of each step, is contemplated as being not particularly limited unless otherwise explicitly described as such herein.

Other features and advantages of the invention will be apparent from the following description of the preferred embodiments thereof, and from the claims. All references cited herein are hereby incorporated by reference.

Arbuscular Mycorrhizal Fungi (AMF, or AM Fungi)

Soil is known to contain in various climates and geographic locations any number of fungi. One widely dispersed group of fungi garnering much attention in the agricultural and scientific communities in general are mycorrhizal fungi. Mycorrhizal fungi are found worldwide and are known to form a symbiotic or mutualistic association with land plants. Several known mycorrhizae have been characterized, among them the arbuscular mycorrhizal fungi, or AMF, sometimes referred to herein as AM fungi. The AM fungi colonize cortical cells of roots in most of the native plants and agricultural crops in the world. However, AM fungi are different from other mycorrhizal fungi because AM fungi grow in the form of structures surrounding and penetrating cortical cells of roots of host plants. These structures of AM fungi penetrating the cells of host plants are often in the form of a tree-like structure called an arbuscule that resides inside the cortical cells of the root. Nutrient exchange occurs between the host plant and the AM fungi at these arbuscular structure junctions with plant cortical cells. (See, Selvakumar et al., *J. App. Microbiol.*, 124(6):1556-1565, 2018; and Parniske, M., *Nature Rev. Microbiol.*, 6:763-775, 2008). An arbuscule is a microscopically observed fungal organ unique to the AM fungi. The structure of the arbuscule is in the form of a very fine branching of the fungi within the plant host cells of the root cortex.

The vast majority of land plants are mycorrhizal of one type or another. There are seven recognized types of mycorrhizae. (Bellgard and Williams, 2011, Ibid.). The majority of plants are of the AM type, but among these are plants that are obligately mycorrhizal and others that are facultatively mycorrhizal. There are a few plant families that are nonmycorrhizal with regard to any mycorrhizal association. (Wang and Qiu, 2006, Ibid.).

Previously these fungi were known as vesicular arbuscular fungi, or VAM, because it was thought that all members formed vesicles as well as arbuscules. However, it is now known that many species of AMF do not form vesicles, but all form arbuscules.

It is straight forward to identify from spore characteristics those AM fungi that are members the class Glomeromycetes, particularly those in the orders Glomerales and Diversisporales. However, these taxonomic names are fairly recent (Schüßler et al., 2010, "The Glomeromycota. A species list with new families and new genera," A. Schüßler & C. Walker, Gloucester), and since have been modified (Redecker et al., "Mycorrhiza," 23:515-531, 2013). General identification of AMF belonging to these two orders can be traced back to one of the first published taxonomies (Gerdemann, 1971, Misc. Pub., 1189, USDA-FS).

Taxonomy of the AM fungi have consistently been revised since their discovery around 100 years ago. At one time these fungi were considered to be members of the Phycomycetes and all in the family Endogonaceae (Gerdemann and Trappe. 1974. Mycologia Memoir 5:1-76). Several other taxonomic revisions placed these differently, each based on information that AM fungi were increasingly phylogenetically older than previously thought. Currently they now have phylum status of their own, being assigned to the Glomeromycota. (Redecker et al., 2013, Ibid.). The AM fungi are found in the fossil record dating back at least 590 million years. (Bellgard and Williams, 2011, Ibid.). The evolution of these fungi parallels that of land plants.

Growth of AMF is measured or detected by an increase in spore numbers and increase in infection percentage of roots. Growth of AMF is a topic of much debate and research within the field since AMF are known to be very beneficial to crop plants and plants in general. A steady and large supply of AMF for the purposes of colonizing crop plants has long been sought but difficult to achieve due to the special and specific conditions needed to culture AMF.

The Role of Elemental Phosphorous, P

Much is being discovered about the chemistry and biochemistry of phosphorus that is either new information or ignored information. (White and Metcalf, 2007, Ibid.). Taken as a whole, newly discovered organic phosphorus compounds, the various phosphorus compounds with reduced valences, and the organic compounds that incorporated low valence phosphorus, result in a complicated phosphorus scenario. This is an indication that our scientific understanding of phosphorus and its role in ecology is likely incomplete and will continue to change and grow.

To further characterize the central concepts of phosphorus, a phosphorus cycle was developed based on first principles of oxidation and reduction, as shown in FIG. 1. In FIG. 1, the P cycle is depicted as strictly inorganic; however, it is well established that there are numerous organic compounds that incorporate many of the various valence P forms. (See, White and Metcalf, 2007, Ibid).

Elemental phosphorus is peculiar in that it has three or four allotropes. (Corbridge, 2013, Ibid.). The most common, white and red, are insoluble in water (Lide, 1998-1999, Ibid.), are flammable, and probably are not biologically available. Black phosphorus is also chemically inert and is nonflammable. Given the insolubility or inert properties of these three allotropes of P, it seems unlikely that they are important in the P cycle. However, phosphine is biologically formed. (White and Metcalf, 2007, Ibid.). The pathway to phosphine from phosphate passes through elemental P. Perhaps the intermediary is another allotrope of P; however, the path to complete oxidation of $H_3P$ (phosphine) passes through elemental P to form hypophosphite ($PO_2^{-3}$). Hypophosphite can be oxidized to phosphite by bacteria, e.g., *Pseudomonas stutzeri*. (White and Metcalf, 2007, Ibid.). Oxidation of phosphite to phosphate has been demonstrated for many microorganisms, e.g., *Desulfotignum phosphidtoxidans, Alcaligenes faecalis, Escherichia coli, Xanthobacter flavus*, as well as *P. stutzeri*, although the pathways and enzyme systems vary between organisms (White and Metcalf, 2007, Ibid.). *P. stutzeri* has been shown to derive energy from this transformation including generation of $NADH_2$, which would be very important in oxidative phosphorylation. It is likely that other organisms listed here are also capable of this transformation. "Given that even greater amounts of energy would be available from the oxidation of more-reduced P compounds, [these discoveries]

sets the stage for the isolation of many new types of P-oxidizing microorganisms . . . " (White and Metcalf, 2007, Ibid.).

In addition to the observation of elemental phosphorus in soils, there is increasing evidence for the production of the highly reduced phosphorus compound, phosphine ($H_3P$), in various environmental situations including its generation in soils. (Coyne, M. S., 1999, "Soil Microbiology: An Exploratory Approach," Delmar Publishers), and sewage. (Devai et al., Nature, 333:343-345, 1988). The oxidation of phosphine is spontaneous when in contact with oxygen. Phosphine production during decomposition of organic materials, especially in bog materials (Histosols) has been confirmed recently using modern methods, but reports date back more than a hundred years. (White and Medcalf, 2007, Ibid.).

The significance of these observations is that phosphine is produced in some soils and under other highly reduced circumstances, e.g., in sewage treatment. Indeed, other reports exist of the finding of naturally-occurring phosphine. It is possible even under bog conditions at high elevation in relatively cold soils to find phosphine, e.g., conditions found in Yellowstone National Park, Cryaquepts. (See, mapping unit 353Z, Rodman et al., 1996, "Soils of Yellowstone National Park," Yellowstone Center for Resources, Yellowstone National Park, Wyoming, YCR-NRSR-96-2). Cryaquepts have an aquic moisture regime comprising water saturation, oxygen depletion, and chemical reduction (Buol et al., "Soil Genesis and Classification.," $5^{th}$ Ed., 2003, Wiley-Blackwell, Iowa State University Press) and a cryic temperature regime (mean annual temperature at 50 cm of less than 8° C., but higher than 0° C.). (See, Rieger, S., 1983, "The Genesis and Classification of Cold Soils," Academic Press, New York).

These observations therefore suggest that there is a cycling of phosphorus within soils based on oxidation and reduction. (See, White and Medcalf, 2007, Ibid.). That some bacteria can utilize phosphite as an energy source adds credence to the possibility of a phosphorus cycle based on oxidation and reduction. There is increasingly more published information that shows phosphine ($H_3P$) being evolved especially from wet soils.

It is hypothesized herein that the AMF, generally thought to be obligately associated with plants, acquire nutrition other than by heretofore known pathways. One possibility is that an association has developed between bacteria that oxidize phosphite and AM fungi where the fungi secure some of the energy available through this association. Mosse and others have observed such an association. (Mosse, B., "The establishment of vesicular-arbuscular mycorrhiza under aseptic conditions," J. General Microbiology, 27:509-520, 1962). Other microorganisms, including other fungi, have been observed to be intimately associated with AM fungi including bacteria-like organelles imbedded in the cytoplasm of AM fungal spores. (See, Bagyaraj, J., "VA Mycorrhizae," Powell, C. and Bagyaraj J. Eds., Ch. 7, pp. 131-154, CRC Press, 1984). Here this is named the "microbial association hypothesis."

Culturing of Arbuscular Mycorrhizal Fungi

All known organisms require a carbon source for organismic structure and an energy source for fundamental metabolism. Certainly, other nutrients are required as well, e.g., nitrogen, phosphorus, and several micronutrients. Eukaryotic and many prokaryotic organisms use carbon not only for structure but also for energy acquisition. The most ancient organisms, bacteria in the Archaea Domain, are capable of splitting their carbon and energy acquisition. Carbon comes often from fixing of carbon dioxide but some may also secure carbon from fixed carbon sources. Energy is derived from oxidation of inorganic compounds like ammonium, hydrogen sulfide, ferrous iron, and many others. Recently, it has been observed that some bacteria can secure energy from the oxidation of phosphite to phosphate. (See, White and Metcalf, 2007, Ibid.).

One of the as yet unchallenged characteristics of AMF is that they are strictly obligate biotrophs. The methodologies described herein questions this general assumption within the field that AM fungi can only grow and reproduce when in association with vascular plant hosts. Indeed, there is a taxonomy of plants that addresses their capacity to associate with AM fungi.

The present application provides materials and methodologies suggesting an alternative hypothesis to the "microbial association hypothesis" described above. That is, it is postulated herein that the AM fungi are capable of a free-living lifestyle because they are able to utilize reduced phosphorous compounds (such as phosphite) as an energy source. Because reduced phosphorus is rare in terrestrial environments, AM fungi have developed the capacity to secure energy from their associations with plants.

This hypothesis named here the "free-living hypothesis" suggests that the AM fungi, during their evolutionary development, must have had access to considerably more reduced compounds of phosphorus in terrestrial or even aquatic systems than are present today. (Additional support for this hypothesis can be found in, for instance, Gluck, A., Am. Scientist, 43:479-489, 1955). The crux is that in an archaic biosphere that was anoxic, phosphorus existed in numerous reduced states and as plants evolved and the Earth's atmosphere became increasing oxygen rich, phosphorus became increasingly dominated by highly oxidized forms, mostly as phosphates.

Provided herein are descriptions of methods showing that AM fungi can indeed be grown in the absence of plants or plant material, i.e., devoid of a symbiotic relationship cognate. The key additive, it has been surprisingly found herein, is phosphite. Thus, described herein are methods of growing AM fungi in culture, i.e., within a controlled environment, on small or large scales, in the absence of plant material. The key energy-dependent component added to the AM fungi culture is a reduced form of phosphorous, such as phosphite.

It can be immediately grasped by one of skill that this surprising finding potentially has enormous agricultural and commercial potential for making much more efficient the large scale production of AM fungi. The AM fungi cultures would then be utilizable anywhere globally, upon transport, to assist in the growth of commercial plant crops of all types that benefit from AM fungi symbiosis anywhere in the world. Upscaling the methodologies and compositions described herein from laboratory to commercial levels allows this new discovery to be used to enhance growth of annual commercial crops, e.g., cotton, corn, wheat, pecans, apples, peaches, horticultural plants, as well as some forest species, e.g., aspen, cottonwood, and birch. The methods and compositions described herein also has immediate application in reclamation especially of drastically disturbed lands, e.g., open pit mines. Supplementing existing soils with a phosphorous energy element, such as phosphite, as described herein enhances the native population of AM fungi and thus provides in turn a more favorable growth environment for plants.

AM fungi inoculum production by way of the presently described methods and compositions is achieved without use of a plant host or any detectable levels of live plant material. Nonetheless, the methods still require soil as the base media.

Active AM Fungal Culture

Starting material for the methods described herein include initial active cultures of AM fungi. The amount of starting culture, or seeding culture, is not particularly important so long as there is sufficient quantity of live AM fungi to allow reproduction of further generations upon incubation under the conditions described below. Amounts of active culture useful in the described methods include those, for instance, described in the Examples provided below, including particularly Example 4.

In one embodiment, the amount of AM fungi useful as an initial culture is about 4 AMF spores per gram of soil after inoculation of the soil with the active culture of AMF. In another embodiment, the amount of AMF in the provided culture is from 1 to 10 AMF spores per gram of soil, or 1 to 9, or 1 to 8, or 1 to 7, or 1 to 6, or 1 to 5, or 2 to 4, or 3 to 5, or 4 to 8 spores per gram of soil. In some embodiments the number of spores of AMF is about 8 spores per gram of soil after inoculation of the soil. In other embodiments, the number of spores of AMF is about 4 to about 8 spores per gram of soil after inoculation, or about 2 to about 10 spores per gram of soil after inoculation. In other embodiments, the number of spores of AMF is at least 4 or at least 8 spores per gram of soil after inoculation It is understood herein that the soil in these instances is possesses a moisture content of about 5.0 wt % to about 7 wt %, or about 5.8 wt %, when air dry to about 10 wt % to about 15 wt %, or about 13 wt %, after water is added and comprises added filler, such as sand, in an amount of about 50 wt % to 60 wt %, or about 51.6 wt %.

In some instances, all of the spores are capable of reproduction, but this is not necessarily required. In some instances, some of the spores are not capable of reproduction, i.e., are not competent. In some embodiments, at least a percentage of the spores are dormant. In other words, the active culture sometimes comprises dormant or reproduction incompetent spores and is not comprised solely of 100% pure reproduction competent active spores. For instance, it is known that nearly all spores are dormant to some degree, i.e., possessing a very low rate of metabolism. Likewise, not all spores are able to germinate, for multiple reasons. Thus, when methods described herein require provision of active AM fungi cultures, it is understood that a percentage of those cultures comprise in some embodiments dormant, inactive, or otherwise incompetent spores, i.e., spores not capable of germination and reproduction. In idea embodiments, the AM fungi culture comprises 100% active spores. In some embodiments the active culture provided in the described methods is 90% active, 80% active, 70% active, 60% active or optionally sometimes only 50% active.

Active cultures of AMF are available commercially from many different sources, for instance from The International Culture Collection of (Vesicular) Arbuscular Mycorrhizae (INVAM, invam.wvu.edu, Director Matt Kasson) maintained at the University of West Virginia in Morgantown, WV, US. Several commercial sources sell active cultures of AMF. Such cultures are available as dried whole inoculum, cleaned and washed spores, and in customized mixtures of isolates. Embodiments of the methods described herein contemplate providing active cultures of AMF in any convenient form as described here. Active cultures are in some embodiments in other solid media form, such as an agar or similar solid or semi-solid culture medium. In some embodiments, the culture is contained in a soil or soil mixture optionally including sand as a component of the initial culture. In some embodiments, the commercially obtained active AMF culture comprises soil containing 80 wt % sand, 70 wt % sand, 60 wt % sand, 50 wt %, sand, 40 wt % sand, 30 wt % sand, 20 wt % sand, or as little as 10 wt % sand, or no detectable sand at all. Optionally the substrate (soil and/or sand) in which the active AMF culture is obtained comprises other supplements and additives known to promote the health and maintenance of AMF spores. Additionally, it is known that AMF are able to be cultured in soilless systems. (See, for instance, US Pat. App. Pub. No. 2019/0216025, incorporated herein by reference). It is contemplated herein that the active AMF culture is obtained from a soilless culturing system or alternatively from a soil-based culture.

The active culture of AMF comprises any number of known AMF. As is well known in the art, AMF spores are distinguished by their size (less than about 10 μm to about 1000 μm), color, surface appearance, hyphal attachment, and mode of formation. In one embodiment, AMF do not comprise one or more of the following: ectomycorrhizae, ericoid, orchid mycorrhizae, arbutoid mycorrhizae, ectendo mycorrhizae, and monotropoid mycorrhizae, and a combination thereof. In another embodiment, the AMF culture comprises mycorrhizae mycobionts that form arbuscules with symbiotic plants. In one embodiment, the active culture of AMF comprises one or more *mycorrhiza* species from genera including *Paraglomus, Archaeospora, Geosiphon, Ambispora, Sclerocystis, Rhizophagus, Septoglomus, Funneliformis, Glomus, Claroideoglomus, Racocetra, Cetraspora, Dentiscutata, Gigaspora, Scutellospora, Pacispora, Acaulspora*, and *Redeckera*. In other embodiments, the active culture comprises one or more *mycorrhiza* species from families including Paraglomeraceae, Archaeosporaceae, Geosiphonaceae, Ambiscporaceae, Glomoeraceae, Claroideoglomeraceae, Gigasporaceae, Pacisporaceae, Acaulosporaceae, and Diversisporaceae. In another embodiment, the AMF culture comprises one or more *mycorrhiza* species including at least *Claroideoglomus etunicatum* (*Glomus etunicatum*), *Rhizophagus clarus* (*Glomus clarum*), *Rhizophagus intraradices* (*Glomus intraradices*), and *Septoglomus deserticola* (*Glomus deserticola*).

Often such active cultures when obtained commercially are provided in an appropriate shipping container, such as a Styrofoam box, a cardboard box, a glass container, or other suitable vessel for transportation of live AMF cultures. The culture is also in some embodiments obtained directly from the described methods. That is, upon initially performing the described methods with an active culture, the active culture needed for further methods described herein are obtained therefrom.

Active cultures are also in some embodiments obtained directly from native soil. Methods of isolation and quantification of active AMF cultures found in soils around the world are known and specifically incorporated herein by reference. Thus, active AMF cultures are in some embodiments obtained directly from the soil in which the method will be performed by the person performing the method. That is, the active AMF culture is in some embodiments not a commercially obtainable culture but rather, one that is obtained from existing plant roots and other plant material, for instance directly from the site at which the method is to be performed. Thus, providing the active culture of AMF in the described methods herein in some embodiments includes other steps of first isolating AMF from native soils and optionally quantifying the isolated AMF from the native soils prior to use according to the methods described herein.

Soils or AMF Culture Medium

Central to the methods described herein is the provision of soil comprising phosphorous. The soil type and quantity is not particularly limited but must be of a type known to be permissive to AMF growth and reproduction from spores. Likewise, the amount and type of phosphorous to be added to the soil, or with which the soil is supplemented, is also not particularly limited but must be sufficient, as shown in the examples below, to support AMF spore germination and reproduction. The soil is in some embodiments supplemented with other fillers, additives, and supplements as desired. However, the soil comprises in some embodiments no pesticides, insecticides, fungicides, or other chemicals toxic to fungi or that would otherwise preclude spore germination and growth. That is to say, in some method embodiments described herein, an additional step of removing such toxins from the soil is first contemplated in order to ensure the active AMF culture is able to grow in the media. Soil is in some instances herein referred to as growth media, media, or medium.

In some embodiments, the soil into which the active culture of AMF is inoculated is one or more soil types selected from Entisols, Aridisols, Inceptisols, Alfisols, Spodosols, Ultisols, Oxisols, Mollisols, Vertisols, Histosols, Gelisols, and Andisols, and combinations or mixtures thereof. In a particular embodiment, the soil is Morset series soil or Lymanson series, or a combination or mixture thereof. In a more particular embodiment of the methods described herein, the soil is a member of the fine-loamy mixed Argic Cryoborolls.

Soils are in some instances amended with a phosphorous compound, such as phosphite, to enhance development and growth of AM fungal populations. Amendments of phosphorous include, but are not limited to, phosphate anion $PO_4^{3-}$ and/or phosphite anion $PO_3^{3-}$, or potassium salts thereof, such as, $K_2HPO_4$ and/or $K_2HPO_3$. Other salts of phosphorous compounds are also contemplated herein. Thus, potassium salts are one embodiment of the described methods, but other known and commercially available salts of phosphorous compounds known to those in the art are also contemplated instead of or in addition to potassium salts. Other known phosphorous compounds include, for instance, monoammonium phosphate, diammonium phosphate, rock phosphate, ammonium polyphosphate, superphosphate, and the like. Such phosphorous amendments to the soil are in some embodiments in the form of a solid and in some embodiments are liquid. All such phosphorous compounds are available commercially from numerous sources throughout the world and are quite common.

The levels of phosphorous compounds present in the soil is not particularly limited but are of a sufficient quantity to support AMF reproduction and growth. The surprising finding presented in the examples provided below was that elemental P, of any quantity, was actually found to be naturally occurring in soil. This surprising finding led to the hypothesis that a phosphorus cycle based on oxidation/ reduction exists naturally in soil and that this cycle could play a beneficial role in the life cycle and growth of AMF. Thus, the methodologies described herein include, optionally, the use of soil comprising some form of phosphorous. For instance, an average elemental P content of about 2.6 ng P per gram of oven dried soil (Table 1) was apparent in the surface soil with much less appearing at lower depths. Thus, in some embodiments, the amount of phosphorous typically found in the soil is between 1.0 ng and 100 ng phosphorous compounds per gram of oven dried soil having an average moisture content of about 0.65 wt % to about 4.46 wt %. Where it is found or detected that the amount of phosphorous in the soil is lower than these ranges, in some embodiments, optionally phosphorous is added to the soil to bring the amount of phosphorous to within the ranges described herein, thereby beneficially influencing the life cycle and growth of AMF therein.

Amendment of the soil to include phosphorous compounds means to physically add the phosphorous compounds to the soil and then to physically mix, by hand or other mechanical means, the soil with the amendment so that a relatively or mostly uniform distribution of the amendment throughout the soil is achieved.

Other amendments that are optionally contemplated as being added to the soil or AMF medium include, for instance, calcium, sulfur, and/or magnesium, or mixtures thereof.

The soils used in the methods described herein are in some embodiments optionally comprise various carbon sources. Such carbon sources found naturally occurring in soil are typically a carbohydrate, such as glucose, xylose, sucrose, lactose, fructose, trehalose, galactose, mannose, mannitol, sorbose, ribose, maltose and complex carbohydrates such cellulose, various hemicelluloses, and starch (including amyloses and amylopectin); organic acids such as fulvic acids, humic acids, acetic acid, fumaric acid, citric acid, propionic acid, malic acid, malonic acid, and pyruvic acid; alcohols such as ethanol, propanol, butanol, pentanol, hexanol, erythritol, isobutanol, xylitol, and glycerol; fats and fatty acids includes lipids (neutral lipids, glycolipids, polar lipids) as well as a diversity of saturated, monosaturated and polyunsaturated fats, etc. Other carbon sources include, but are not limited to, arbutin, raffinose, gluconate, citrate and hydrolyzed cellulosic material. Soil organics may also include various lignins. These generally high molecular weight molecules have amorphous properties and may include phenolic, heterocyclic phenols, methoxy side chains, hydroxyl side chains, aliphatic side chains and others. In instances where the soil is found to be devoid of sufficient carbon, carbon sources as described above are optionally added to the soil as needed to promote growth.

In one embodiment, growth factors and trace nutrients for microorganisms are included in the soil as additives. Inorganic nutrients, including trace elements such as iron, zinc, potassium, calcium, copper, manganese, molybdenum, and cobalt; phosphorous, such as from phosphates; and other growth stimulating components are optionally included in the soil. Furthermore, sources of vitamins, essential amino acids, and microelements are in some embodiments amended to the soil, which include, for example, those found in the form of flours or meals, such as corn flour, or in the form of extracts, such as yeast extract, potato extract, beef extract, soybean extract, banana peel extract, and the like, or in purified forms. Amino acids such as, for example, those useful for biosynthesis of proteins, are also contemplated as being added, in some embodiments.

In certain embodiments contemplated herein, inorganic or mineral salts are optionally amended to the soil. Inorganic salts include, for example, potassium dihydrogen phosphate, dipotassium hydrogen phosphate, disodium hydrogen phosphate, magnesium sulfate, magnesium chloride, iron sulfate, iron chloride, manganese sulfate, manganese chloride, zinc sulfate, copper sulfate, calcium chloride, calcium carbonate, sodium carbonate. These inorganic salts are contemplated as being used independently or in a combination of two or more.

The soil provided in the methods described herein, in certain embodiments, further comprise sources of nitrogen. The nitrogen source is, for example, in an inorganic form, such as potassium nitrate, ammonium nitrate, ammonium sulfate, ammonium phosphate, ammonia, urea, and ammonium chloride, or an organic form such as proteins, amino acids, yeast extracts, yeast autolysates, peptones, casein hydrolysate, and legume derived proteins. These nitrogen sources are contemplated as being used independently or in a combination of two or more.

Each of the various components should be present in concentrations effective to promote AMF production. It will be apparent to one of skill in the art that nutrient concentration, moisture content, pH, and the like are able to be modulated to optimize growth for a particular AMF.

The soil employed in the methods described herein in some embodiments comprises sand. Just as in the active culture of AMF supplied commercially or otherwise available to potential users, the soil medium in which the AMF culture is inoculated also in some embodiments comprises sand. In some embodiments, the soil comprises 80 wt % sand, 70 wt % sand, 60 wt % sand, 50 wt %, sand, 40 wt % sand, 30 wt % sand, 20 wt % sand, or as little as 10 wt % sand, or no detectable sand at all.

The soil medium, as shown below in the example section, possesses generally a pH of from 5.3 to 7.9 or 7.3 to 7.9. In other embodiments, the soil has a pH of 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, or 8.0. The pH is in some embodiments between 7.0 and 8.0, or 6.5 to 8.0, or 6.0 to 8.0, or 7.0 to 7.9, or 7.1 to 7.8, or 7.2 to 7.7, or 7.3 to 7.6, or 7.5.

The soils described herein as suitable medium for the inoculation and growth of active AMF in various embodiments also include organic carbon of varying amounts. The phrase "total organic carbon," or alternately referred to herein as "organic carbon" is the amount of carbon found in an organic compound and is often determined by dry combustion or by dichromate redox, and comprises dead and decaying remains of plants, animals, microorganisms, and associated metabolic waste thereof. Other methods of measurement are known, such as acidification, oxidation, combustion, high temperature catalytic oxidation, photo-oxidation, ultraviolet/persulfate oxidation, conductivity, non-dispersive infrared, and the like. Generally, TOC in a sample is indicative of carbon atoms bound covalently in organic compounds. Examples of organic matter are plant or animal based, or synthetic substances containing carbon and other elements defining organic compounds. TOC and organic carbon does not include inorganic compounds comprising carbon. A measurement of TOC does not provide information about which specific organic carbon compounds are in the sample, but instead provides a quantitation of the amount of organic compound in total in a sample in general of any type, combined into one numerical value or estimated value.

Thus, in some embodiments, the soil described herein for use in the methods described herein comprises a total organic carbon (TOC) content of greater than 0.5 wt % and less than 4.0 wt %, wherein the organic matter is free of living plant material, wherein organic matter is determined by dry combustion or by dichromate redox, and wherein organic matter comprises dead and decaying remains of plants, animals, microorganisms, and associated metabolic waste thereof. In other embodiments, the soil TOC is between 0.75 wt % and 3.5 wt %, between 1.0 wt % and 3.0 wt %, and in some embodiments from 0.5 wt % to 8.0 wt %. It is to be understood herein that TOC does not include living plant material, such as live plant roots, and the like.

In some embodiments, the soil provided in the methods described herein is first dried for a period of time prior to inoculation. Methods of drying soil are known in the art and include, for instance, evaporation at ambient temperature with or without the aid of turning in combination optionally with air movement devices such as fans, blowers, and the like. Another known method of soil drying includes exposure of the soil to heat. Air drying is conducted for periods of up to several weeks depending on the amount of soil to be dried. It is well understood to those in the art that the more soil there is to be dried, the longer air drying will require in order to achieve the desired moisture content. To dry soil by application of heat comprises exposing soil to a heat source for a period of time. The intensity of the heat source and the amount of time needed depends directly on the amount of soil to be dried, the amount of the soil that is exposed to air, and the desired moisture content. Other variables in the drying process include mechanical manipulation of the soil as it is dried, mixing of the soil during the drying process, etc.

By convention, soil moisture is expressed as a percentage of the weight of water in a given sample divided by the weight of the oven dried soil. Oven dried soil was obtained by heating small soil samples at 105° C. for 24 hours or to constant weight. (See, Reynolds, W. D. and Topp, G. C., "Soil Water Analysis: Principles and Parameters," In: Carter and Gregorich, "Soil Sampling and Methods of Analysis," CRC Press, Boca Raton, FL, 2008, pp. 913-938). It is contemplated herein that soil in some embodiments is dried to 0.5 wt % moisture content, 0.6 wt %, 0.7 wt %, 0.8 wt %, 0.9 wt %, 1.0 wt %, 1.5 wt %, 2.0 wt %, 2.5 wt %, 3.0 wt %, 3.5 wt %, 4.0 wt %, 4.5 wt %, 5.0 wt %, 5.5 wt %, or 10 wt %.

Aside from the gravimetric method (with oven heating) described above, other methods for determining soil moisture are time-domain reflectometry, ground penetrating radar, impedance and capacitance methods. (See, Topp, G. C., Parkin G. W., and Ferre' Ty P. A., "Soil Water Content," In: Carter and Gregorich, "Soil Sampling and Methods of Analysis," CRC Press, Boca Raton, FL, 2008, pp. 939-961).

Removal of Living Plant Material from the Soil

In specific embodiments described herein, the soil comprises no living plant material or optionally no detectable level of living plant material. Plant material includes, for instance, all living plant tissues including roots, shoots, buds, leaves, nodes, stems, petioles, flowers, seeds, and components or parts, or cells thereof, that are replication competent, i.e., capable of sustaining life and growing under proper conditions. In some embodiments, the soil comprises endogenous plant material, if naturally present. In some embodiments, no living plant material is added or amended to the soil.

In some embodiments, any and all living plant material is actively removed from the soil prior to inoculation with the active AMF culture. Living or alive plant material is removed from soils by any of the known and described methods in the literature within the field. In one embodiment, removing or eliminating all detectable living plant material from the soil comprises contacting the soil with steam, UV radiation, and/or ethylene oxide. Removing living plant material from the soil comprises removal of, elimination of, or killing of, all detectable amounts of living plant material within the soil or medium. It is to be understood that the ability to detect living plant material, on a cell by cell basis, is challenging especially in soils, though methodology exists to achieve this task. Thus, it is understood and contemplated herein that while these exemplary methods of eliminating living plant material from the soil are typically industry standard and effective to achieve the goal desired, if applied different, these methodologies theoretically are capable of leaving behind undetectable quantities of living plant material in the soil. Thus, elimination of living plant material from the soil comprises eliminating 100%, 99%, 98%, 97%, 96%, 95%, 90%, or even 85% of detectable living plant material from the soil.

As is explained in further detail, below, the focus on living plant material in the presently described methods is to highlight certain surprising and counter-intuitive findings about AMF that are reported for the first time herein. That is, it has surprisingly been discovered that AMF appear to be capable of reproduction and growth without the presence of living plant material or roots of any kind. This exciting finding shows that AMF are capable of growing in medium that is devoid or living plant material, such as roots, meaning that the AMF are capable of deriving all nutritional needs from endogenous sources within the soil other than live plant roots. It has heretofore been accepted as fact that AMF only grow, or are only capable of growing well or in a sustained manner, in the presence of living plant root material. Removal of this requirement presents a marked change and improvement in the culturing and provisioning of AMF to growers and societies around the world reliant on agricultural crops, as well as businesses focused on horticulture, and the like.

Thus, in some embodiments, it is explicitly contemplated herein that the methods described herein meet their intended goals when active AMF cultures are inoculated into medium that is devoid of live plant material, i.e., wherein all detectable traces of living plant material have been removed. In some embodiments, the soil in which the AMF is inoculated, comprises no detectable levels of living plant root material, but optionally comprises other living plant material, such as living plant cells of shoots, buds, leaves, nodes, stems, petioles, flowers, seeds, and components or parts, or cells thereof, that are not plant roots.

Inoculating Soil with AMF Culture

The methods described herein further comprise the step of adding the active culture of AMF to the soil. This step, therefore, includes adding a portion of active culture of AMF to a culture medium capable of sustaining AMF culture growth, such as soil, as described hereinabove. The amount of active culture added to the soil varies depending on the growth conditions and other variables. The different types of AMF within the active culture are described elsewhere above, as are the various soil types and conditions.

Inoculation of the soil with the active AMF culture comprises in some embodiments simply adding the active culture contents to the soil to be inoculated followed by general mechanical mixing of the added culture until the soil is relatively consistent throughout with active AMF culture spores. It should be well understood that depending on the amount of soil to be inoculated and the amount or volume, or type of inoculant, different types of mechanical or physical mixing may be required for varying amounts of time.

The conditions under which the active culture of AMF is added to the AMF medium (soil) varies depending on type of AMF in the active culture, and the like. For instance, the amount of moisture in the air, amount of air circulation, the amount of mechanical mixing, the depth into which the inoculant is inserted into the soil, the amount of distance between inoculation sites, the temperature of the soil, the temperature of the air, the temperature of the active culture of AMF, and such variables are not particularly limited. It is to be understood that the inoculant is in some embodiments thoroughly mixed throughout the soil medium but in other embodiments an amount of active AMF culture is inserted into the soil at specific distances apart from each insertion point and at specific depths that are selected for optimized AMF growth. As described hereinabove, the amount of AMF active culture inserted into the soil at any given insertion point is selected based on optimization of conditions and other known factors contributing to growth using the described methods.

In some embodiments, the active culture of AMF is inoculated into the soil medium in a glass test tube. In other embodiments, the AMF is inoculated into the soil medium in an enclosed greenhouse. In other embodiments, the AMF is inoculated into the soil medium in an open greenhouse. In other embodiments, the AMF is inoculated into the soil medium on a farm or plantation or grove for production of commercial crops of any type. In other embodiments, the AMF is inoculated into the soil medium in a reclamation site. Thus, in some embodiments, the soil is able to be easily mixed with the active culture of AMF but in others the soil cannot be easily mixed such that the active AMF spores are spread uniformly throughout the medium. Thus, the conditions of addition of inoculant to the soil will depend on the downstream use intended for the method, be it crop growth, AMF culture production, reclamation project, or other intended use or application of the technology described herein.

Exposure of Inoculated Soil to Light and Water

After addition of active culture of AMF spores to the soil/medium, the inoculated medium is exposed to water and light to promote AMF propagation and growth. As will be clear to one of skill in the art, the amount of light and water to be added to the inoculated medium/soil depends on many factors, such as the amount of medium/soil, the amount of active AMF culture added to the soil, the amount of live or competent AMF spores in the active culture added to the soil, the temperature of the soil, the general growth conditions of the soil (laboratory vs. natural setting, controlled or uncontrolled), and the like. For instance, if the AMF active culture is added to the soil in a laboratory setting where all moisture and other conditions are controlled, the amount of light and/or water added to the soil with the AMF can be carefully optimized and monitored.

On the other hand, if the AMF culture is added to soil under uncontrolled conditions where the soil is exposed to natural sunlight and rain water or runoff from streams and the like, or fog, or ocean spray, for instance, the amount of light and water added to the inoculated soil will vary widely taking into account the water and light obtained naturally from the open air uncontrolled location in which the inoculation action occurred.

Nonetheless, in certain embodiments where the environmental conditions in which the inoculated soil is contained is controllable, the light added thereto is full spectrum luminous flux light. In certain embodiments, the light is at least 24,000 lumens and directed to the inoculated soil for a period of 8 to 20 hours during a 24 hour period. In other embodiments, the light is between 20,000 and 30,000 lumens, or 10,000 to 20,000 lumens, or 22,000 to 26,000 lumens. In some embodiments the inoculated soil is exposed to the artificial light source for 5 to 24 hours within a 24 hour period, or from 10 to 20 hours, or from 12 to 18 hours, or from 14 to 16 hours, or from 5 to 10 hours during a 24 hour period. In some embodiments, artificial light is used only when natural sunlight does not meet these parameters described herein. In some embodiments, the light comprises a combination of artificial light and natural sunlight.

It is to be understood that the amount of light, the light intensity, the duration of exposure to light, and the wavelength of the light will depend on many variables including, for instance, the exposure of the inoculated soil to natural sunlight, the amount of inoculated soil, the amount of AMF active culture added to the soil, the amount of moisture in the atmosphere, the amount of water added to the inoculated soil, the temperature of the inoculated soil, the temperature of the air above and around the soil, the pH of the soil, and other quantifiable factors. Thus, the amount of light, while in some embodiments is added as described herein, in other embodiments is optimizable to meet the conditions of the specific end use or application of the described methods. In other embodiments no light is added to the soil. That is, in such embodiments the soil is not exposed to any light at all during the growth of the AMF. The fact that in the experimental examples, below, the soil of experimental samples containing no plant material were exposed to light was the result merely of carefully planned experiments following basic scientific principles, i.e., modification of only a single variable at a time between experiments. Thus, since positive control samples including plant material were exposed to sunlight to maintain said plant material, experimental samples containing no plant material were also exposed to sunlight to maintain standard and uniform growing conditions for each set of samples. That being said, it is to be understood that in fact, since AMF have been found to grow without any plant material present, in actuality in certain embodiments the described methods include those in which the soil is not exposed to any light at all. In other words, in certain embodiments, the AMF are grown partially or entirely in the dark.

Likewise, addition of water to the inoculated soil will also vary depending on many factors. While in some embodiments the moisture added to the soil is highly controlled, in others control of water addition is not possible due to the location of the inoculated soil within a field, orchard, reclamation site, and the like.

In one embodiment, in which growth of the AMF in the soil is controlled, water is added initially in a certain amount within a few minutes or hours of inoculation of the soil with the active culture of AMF, and then every third day thereafter. In some embodiments, water is added every day, or every other day, or every fourth day, or twice per week, or several times per month.

In various controlled aspects of the methods described herein water is added in an initial amount of 400 mL water per 3,055 g of soil, and then 100 mL per 3,055 g of soil every third day thereafter. It is to be understood that grams of soil in this instance is referencing soil possessing a moisture content of about 5 wt % (dry) to about 15 wt % (with added water), for instance, about 5.8 wt % (dry) or 13 wt % (added water), and an amount of added sand of between 50 wt % and 75 wt %, for instance, about 51.6 wt %. In other embodiments, the water is added in an amount of between 100 and 800 mL per 3,055 g of soil on the first day, between 150 and 700 mL, between 200 and 600 mL, between 300 mL and 500 mL per 3,055 g of soil in the first day, and optionally every day or every other day thereafter. In another embodiment, after the initial watering, a lesser amount of water is added to the inoculated soil 1, 2, 3, 4, or 5 days after inoculation of the soil. The lesser amount of water, in some embodiments, is between 10 mL and 500 mL of water per 3,055 g of soil, or between 50 mL and 250 mL, or between 75 mL and 125 mL, or between about 90 mL and 110 mL, per 3,055 g soil. This watering regimen is optionally followed for several weeks, months, or even a year until the desired amount of active AMF is deemed to be recoverable from the soil.

It is to be understood that upon completion of the methods described herein, the active AMF in the inoculated soil is then recovered. Various methods of recovery of active AMF from soil are known in the art and include, for example, the sucrose flotation method (Allen, M. F., Moore, T. S., Christensen, M., and Stanton, N., 1979, "Growth of vesicular-arbuscular mycorrhizal and nonmycorrhizal *Bouteloua gracilis* in a defined medium," *Mycologia,* 71, 666-669), and the sieving, decanting, and sucrose technique (Dalpe' Y, and Hamel C., 2008, "Arbuscular Mycorrhizae," In: Carter and Gregorich, "Soil Sampling and Methods of Analysis," CRC Press, Boca Raton, FL, 2008, pp. 355-377). The recovered active AMF are then in some embodiments added to crops, orchards, native plants, and other root systems to improve growth, as described herein, and with methods known in the art for supplement of growing plants, crops, trees, and the like.

Uses of Active AMF in Reclamation and Applications of Live AMF Cultures

Upon following the methods described herein, what is obtained as the end product is propagated live cultures of AMF. The propagated live AMF are then optionally isolated, in some embodiments, to the degree desired, and employed in follow-on end uses or applications, such as to promote growth of commercial crops, horticulturally important or desired flowers and plants, trees, plantlets, orchards, and other plants that survive based on an active root system and that are symbiotic partners with AMF. Live AMF have even found utility in mediating growth and health of olive plantations in Spain. (See, Montes-Borrego et al., *PLoS ONE,* 9(5):e96397, 2014). AMF have been found associated with plants in every ecosystem from alpine and tundra to sea level, from rainforests to deserts and on every continent including Antarctica (See, Bellgard and Williams, 2011. Ibid). Aside from being agriculturally important, there are other applications for active AMF including in reclamation and the like.

In strip mining, often soil is stripped and stored (stock piled) for long periods (greater than a year). AM fungi often cannot survive this length of storage in the absence of plants. Phosphite treatment of stored soils could keep these fungi alive until the soil is replaced and plants re-introduced.

Depleted soils exhausted of resources due to over-farming or over-grazing could be in some instances reclaimed by addition of phosphorous compounds, such as phosphite, to enhance growth of any remaining endogenous AMF in those depleted soils. Such supplementation could theoretically allow succession to proceed more rapidly and perhaps even lead to skipping the successional stage which is usually dominated by invasive non-mycorrhizal plants, such as Russian thistle, Kochia, mustards, and the like. Intensive use of live AMF in plowing of agricultural fields could also yield beneficial results in crop growth. In such a manner, such as in strip farming of, for instance, wheat, fallow strips could be treated with phosphite to enhance growth of endogenous AMF cultures during the time when no plants are present.

Uses of the AMF derived from these methods in horticulture are also contemplated herein. That is, inoculum produced is in some embodiments incorporated into potting soil for production of horticulture stock plants. Potting substrate could be inoculated with live cultures of AMF and treated with low levels of phosphite before soil is bagged, thereby extending shelf life of live AMF in such bagged soils as compared with bagged soils containing no phosphorous compounds.

Addition of live AMF to fertilizers could yield benefits to crops and agriculturally important plants. (See, Adesemoye, et al., *Appl. Microbiol. Biotechnol.,* 85:1-12, 2009). That is, it is well known that over-use of fertilizers can have detrimental side-effects in the surrounding environment through leaching and run-off of nutrients, such as nitrogen and phosphorus. (Id.). Decreasing use of fertilizers around the globe is an important goal to maintain the health of the environment. One such manner in which fertilizer use could be curtailed is by supplementation of fertilizers with live cultures of microbes that beneficially improve plant growth, enhance nutrient availability and uptake, and support overall health of plants by guarding plants from stresses caused by biotic and abiotic factors. (Id.). Such supplementation optionally is accompanied by addition of other beneficial microbes, such as plant growth-promoting rhizobacteria (PGPR), as well as optionally nitrogen-fixing bacteria. Soil compositions comprising AMF, PGPR, and/or nitrogen-fixing bacteria cultures are further enabled by the discoveries described herein concerning growth of AMF in the absence of live plant root material as hosts. Ready availability of active AMF cultures on a large scale logically leads to more accepted and widespread use of such compositions as additions to crop land, leading to decreased need for environmentally harmful levels of fertilizers and an overall improvement in environmental conditions in countries reliant on agricultural commodities. Additionally, it is contemplated that provision of a more readily available source of AMF inoculants will have a similar positive impact on over-use of pesticides. In other words, application of AMF inoculants in crops will create sufficiently healthy plants and growth environments that pesticides use will be curtailed or in some instances even eliminated.

Such benefits noted above, readily envisioned with the methods described herein, positively impact not only large agricultural businesses, but also small-scale and middle-scale agricultural commercial endeavors. (See, for instance, Oviatt, P., Rillig, M., *Plants People Planet*, 3:454-461, 2021). The steady decline of mid-sized farms could be slowed and/or halted through ready availability of large scale quantities of live AMF beneficial to crops and plants grown by these farms. Live AMF culture-derived technologies targeted towards middle agriculture may be more readily investigated through the methods described herein.

The field of crop science as a whole conceivably would benefit from a more readily available source of industrial-scale quantities of live AMF cultures uncomplicated by soil type preferences, host symbiont presence, and such other variables that have caused a bottleneck in such studies due to lack of sufficient quantity and availability of live AMF cultures. Enabling additional scientific research in crop science inevitably will lead to agricultural change and perhaps breakthroughs in environmental sustainability going beyond age-old concepts of crop rotations, cover, and fallow fields. The field of AMF research is stymied by its dogma of obligate symbiont culturing methods. (See, Hui et al., *Plant Diseases and Pests*, 7(2):26-30, 2016). While Hui et al. describe all the various presently accepted modes of large-scale preparations of AMF inoculants, all require and include a host symbiont plant, thus complicating growth conditions.

The presently described methods enable such beneficial practices by making more easily and readily available quantities of live AMF useful in such settings, whereas before this discovery and advancement, the laborious and time-consuming process of culturing AMF precluded widespread use of such cultures in these settings. (See, Adesemoye, et al., Ibid., at page 4, left column, noting that "[i]t is difficult to culture AMF in vitro, and the genetic basis of P solubilization and rhizosphere competence is not well understood."). Hui et al., Ibid., also remark that "due to biotroph and obligate symbiosis of AMF, it is very complex to get high quality inoculants through efficient large-scale production, while unstable performance of mycorrhizal colonization in plant production system and the lack of professional knowledge lead to difficulties in wide use of inoculants at the present stage." (See, Hui et al., Ibid., at page 26, left column, bottom). It is such industry-wide criticism of AMF culturing for which the presently described methods offer a direct solution. The cure of this defect in the lack of AMF material for proper application and research is within reach through application of host plant root-free culturing methods as described herein.

Further modifications and alternative embodiments of various aspects of the methods and systems described herein will be apparent to those skilled in the art in view of this description. Accordingly, this description is to be construed as illustrative only and is for the purpose of teaching those skilled in the art the general manner of carrying out the disclosed methods and systems. It is to be understood that the forms of the disclosed methods and systems shown and described herein are to be taken as examples of embodiments. Elements and materials may be substituted for those illustrated and described herein, parts and processes may be reversed, and certain features of the disclosed methods and systems are capable of being utilized independently, all as would be apparent to one skilled in the art after having the benefit of this description of the disclosed methods and systems. Changes may be made in the elements described herein without departing from the spirit, scope, and theoretical basis of the disclosed methods and systems as described in the following claims.

All of the references cited above, as well as all references cited herein, are incorporated herein by reference in their entireties. The following examples are offered by way of illustration and not by way of limitation.

EXAMPLES

Example 1: Materials and Procedures

The standard bulk (average) density for most soils involved in the following examples was about 1.3 g/ml or about 1.3 g/cc. (See, Plaster, E., "Soil Science and Management," Delmar Publishers, 1996, pp. 39-41).

Soil classification and nomenclature used herein follows the USDA system. (See, "Soil Survey Staff. Soil taxonomy—A Basic System of Soil Classification for Making and Interpreting Soil Surveys," in Agriculture Handbook 436, Washington, D. C., U.S. Government Printing Office, 1999, pp. 1-886).

By convention, soil moisture is expressed as a percentage of the weight of water in a given sample divided by the weight of the oven dried soil. Oven dried soil was obtained by heating soil samples at 105° C. for 24 hours or to constant weight. (See, Reynolds, W. D. and Topp, G. C., "Soil Water Analysis: Principles and Parameters," In: Carter and Gregorich, "Soil Sampling and Methods of Analysis," CRC Press, Boca Raton, FL, 2008, pp. 913-938).

To show statistical significance herein the convention of alpha ($\alpha$) is used. Normally this value is provided directly, although if the value is 0.05 or less, this will be considered statistically significant, and for a value of 0.01 or less, is considered highly statistically significant.

Often P is used to express manifestations of alpha in mathematics and is used generally in the same manner as alpha. However, given that herein "P" indicates phosphorus, the symbol "P" is not used for probability of significance to avoid confusion.

AM fungal inoculum was obtained from The International Culture Collection of (Vesicular) Arbuscular Mycorrhizae (INVAM, invam.wvu.edu, Director Matt Kasson) maintained at the University of West Virginia in Morgantown, WV, US.

All other reagents and the like, unless otherwise noted, were obtained from Sigma Aldrich, St. Louis, MO.

Example 2: Quantitation of Elemental Phosphorus in Rangeland Soils

The purpose of this example is to determine the presence and amount of elemental phosphorous in rangeland soil. Surprisingly, elemental phosphorous was found to be naturally present in detectable quantities in rangeland soils.

A survey was conducted for elemental phosphorus as well as the major oxidation product of phosphorus oxidation, phosphate, in an area of Wyoming (41°05' N and 105°26' W). This area was selected since a white phosphorous spill was reported here. The spill resulted in several days of fires caused by the white phosphorous spill.

Vegetation across all sample sites was similar and described as grasses, forbes, and shrubs of upland range. Vascular plants included Gooseberry and currant (*Ribes* spp), Penstamon (*Penstamon* spp), dry land grasses (*Pascopyron* and *Poa* spp), paintbrush (*Castellija* spp), lupine (*Lupinus* spp), bitter brush (*Purshia tridentata*), rose (*Rosa woodsii*), onion (*Allium* spp), primrose (*Oenothera* spp), and cactus (*Mammallaria* spp).

The period of time when air temperatures are above the freezing point of water is fairly short (60 to 90 days per year) since the site is at fairly high elevation (2,440 meters). Soils at the site (Rogert, rock outcrop association) are well drained, of mostly coarse textures and are classified as Loamy-skeletal, mixed Lithic Cryoborolls. (See, Reckner R., "Soil Survey of Albany County Area, Wyoming," U.S. Government Printing Office, 1997, p. 540, map 80).

Control samples were taken in several locations, including: (a) about 400 meters up-wind of the derailment site (NW), (b) in a drainage separated from the spill site by a ridge, and (c) at an elevation about 5 meters higher than the spill site. Soils from the control sampling sites were well drained, in relatively arid rangelands having native vegetation composed of shrubs and grasses. A further five control samples were obtained along a south to north transect with an interval of 30 meters between sampling sites. Sampling was conducted by removing five one kilogram samples from the surface to 15 cm below surface of each site, mixed, and a 1 kg subsample removed therefrom for quantitative analysis. Subsurface samples were extracted with a soil auger.

Analysis for elemental phosphorus was performed by weighing out 25 g of soil into a 250 ml Erlenmeyer flask. Sixty mL deionized water and 6 mL isooctane (2, 2, 4-trimethyl pentane) was added to the flask and the flask agitated for 3 minutes. The contents of the flask were allowed to settle and separate for 2 minutes. All of the isooctane and some of the water and soil slurry was decanted into a separatory funnel, the water drained off, and the isooctane drained into a glass screw cap vial. The extraction was repeated with 6 mL isooctane which was added to the initial aliquot. The vial was then sealed by covering the opening with Teflon tape and replacing the screw cap. Elemental phosphorus content of the extract was determined by gas/liquid chromatography using standard published protocols. (See, Addison et al., *J. Chromatog.*, 47:421-426, 1970).

Results are shown in Table 1. Elemental P is expressed in units of "ng per gram of oven dry soil."

TABLE 1

| Depth (cm) | Texture[1] | pH[3] | Soil Water (%)[4] | P (ng/g soil)[5] | n |
|---|---|---|---|---|---|
| 0 to 15 | Gravelly, Loam[2] | 7.1 ± 0.19 | 2.51 | 2.62 | 5 |
| 15 to 30 | Gravelly, Loam | 7.4 ± 0.04 | 0.64 | 2.38 | 5 |
| 30 to 38 | Gravelly, Loam | 7.4 | 4.25 | 0.36 | 1 |
| 30 to 46 | Coarse material & Sand | 7.4 | 3.31 | 0.26 | 1 |
| 38 to 51 | Coarse material & Sand | 7.4 | 4.63 | 0 | 1 |
| 51 to 91 | Very course gravel | | 4.46 | 0 | |
| 91+ | Consolidated Rock | | | 0.33 | |

Table 1 Notes:
[1]General texture. Nature of material >2 mm diameter and texture of material <2 mm, separated by a comma (,).
[2]Gravelly: >15% but <35% by volume. Standard texture designation modifiers (Schoeneberger et al., Field Book for Describing and Sampling Soils. (Version 2.0 NRCS, National Soil Survey Center, Lincoln, NE, 2002, p. 2-31).
[3]pH was determined on a 1:5 suspension of soil in distilled water. (See, Peech, M., "Hydrogen-ion Activity," In: Black, C. A., "Methods of Soil Analysis," Agronomy 9, *Am. Soc. Agron.*, Madison, WI. 1965, pp 914-926).
[4]Soil water %. Weight of water divided by the weight of dry soil, quantity multiplied by 100. (See, Gardner, W. H., "Water Content," In Black, C. A., "Methods of Soil Analysis," Agronomy 9, *Am. Soc. Agron.*, Madison, WI., 1965, pp 82-127).
[5]Covariance (standard deviation./mean times 100) is 91%. Values ranged from 0.16 to 6.72 ng/g soil in the top 15 cm of soil.

The control samples showed near neutral to slight alkaline pH values throughout the soil profile and low water contents. An average elemental P content of just over 2.6 ng P per gram of oven dried soil (Table 1) was apparent in the surface soil with much less appearing at lower depths. The slight alkalinity of the soil is consistent with the parent materials (granite) and the climate (semi-arid).

As previously reported, it is accepted generally that there should not be any elemental phosphorus in these control samples, not even small amounts of elemental phosphorous. The prevalent reasoning in the literature is that all of the allotropic forms of elemental phosphorus oxidize readily in the presence of oxygen, and that white phosphorus readily oxidizes even at room temperature. (See, Lide, Ibid., p. 4-21). For elemental phosphorous to be present, it is conjectured that the element must be sequestered within the soil matrix probably in aggregates where oxygen does not penetrate. Implied also is that for elemental P to exist in soils at all, there should be a chemical or biochemical mechanism to generate the elemental phosphorous.

Example 3: Quantitation of Soil Phosphate and Phosphite

A field study was established to test whether phosphates and phosphites added to soil impact soil properties including total soil phosphorus as well as extractable soil phosphorus.

The experimental design described herein was also utilized in Examples 4 and 5 (below). This study was established on a native range site in Wyoming located at latitude/longitude 41.32° N and 105.54° W, and is an arid environment averaging 350 mm of annual melted precipitation (roughly half as liquid and half as solid) at an elevation of 2,277 meters (datum mean sea level). The growing season, when temperatures are above 0° C., is approximately 72 days. However, most range plants can tolerate temperatures of -4° C. Using these criteria, the growing season averages approximately 100 days. High temperatures during the growing season (June, July, and August) average 21° C., whereas low temperatures average 3° C.

Soils at the experiment site were of the Wycolo fine sandy loam series and classified as Fine-loamy, mixed Borollic Haplargids. (See, Reckner R., Ibid., p. 540, and map 64).

Native species on the site were mostly grasses and forbs. Plants were western wheatgrass (*Agropyron smithii*. Synonyms: *Elymus smithii, Elytrigia smithii, Pascopyron smithii* (Monson, et al., "Grasses," In: Monson, S. B., Stevens R., and Shaw N. L. (compilers), "Restoring Western Ranges and Wildlands," *Rocky Mtn. Research Sta.*, Fort Collins, CO, USDA-FS, 2004, GTR RMRS-GTR-136, vol. 2. pp. 334-337), scarlet globe mallow (*Spheralcea coccinea*), desert madwort (*Alyssum desitorum*), Kochia (*Kochia* spp), blue grama grass (*Bouteloua gracilis*), and downy brome (*Bromus techtorum*) (Anonymous, Appendices 1 and 2, "Scientific and Common names," In: Monson S. B., Stevens R., N. L. Shaw (Compilers), "Restoring Western Ranges and Wildlands," *Rocky Mtn. Research Sta.*, Fort Collins, CO, USDA-FS, 2004, GTR RMRS-GTR-136, vol 3., pp 847-882).

A soil pit was excavated a meter to the SSE of the plot area. In general, the pit was mostly undecomposed organic debris from 0 to 1 cm depth. Effervescence from this layer was mild (+) using vinegar (a weak acetic acid) indicating low levels of $CaCO_3$ in the substrate. At a depth of 0 to 2 cm, the substrate was mainly organic debris mixed with soil. Effervescence was stronger (++). The material from 2 to 16 cm was A horizon material with many roots and likely organic matter greater than 1%, thus making it a mollic epipedon (a layer at the top of soil horizon that is of at least 1% organic matter and is high in nutrient bases, calcium, potassium, and/or magnesium). Effervescence was moderate (++). At 16 to 36 cm, the material was mainly a CI horizon with some roots and many coarse fragments (25% by weight). Effervescence was very strong (+++++) indicating high levels of $CaCO_3$. From 36 to 56+cm the material was described as a CII horizon, with few roots, few coarse fragments and moderate effervescence (++). The soil temperature at the time of these observations was 14° C. at 50 cm.

Based on the soil pit description and the soil taxonomy, the focus of investigations of soil properties was limited to the top 15 cm of the soil. From a practical standpoint this would not include the undecomposed organic debris at the surface but would include soil from 1 cm to 16 cm. The abundance of roots and presence of organic matter in this horizon strongly suggests most of the biological activity in this soil resides in this horizon. The high effervescence of the CI immediately below suggests that the penetration of water seldom reaches into the CI horizon.

Twelve plots of size 50 cm by 50 cm were established on a homogenous site 2.54 meters (running northeast and southwest) by 4.06 meters (running southeast and northwest). Plant distribution was mostly homogeneous across the entire site, with western wheatgrass dominant. The plots were in four rows with three plots in each row. Within a row plots were 25 cm apart. Rows were 50 cm apart. An experimental unit was one plot. Treatments were replicated three times. Treatments included: controls (no treatment), potassium chloride treatment, potassium phosphate treatment, and potassium phosphite treatment. (See, FIG. 2).

It was necessary to treat these plots with chemical solubilized in water such that the treatments penetrated to 15 cm and not deeper. According to the taxonomy as well as hand texturing of the soil in these plots, the texture of the soil is clayey to loamy, i.e., textural class: clay loam. Soils generally have a void space (air space when the soil is oven dried at 105° C. for 48 hrs) of 50% of initial volume. Consequently, to completely fill the void space with water to 15 cm would require a water depth of 7.5 cm. For a single plot of 0.25 $m^2$ this would require 18,750 mL of water to saturate the soil. However, using this much water would result in free water (gravitational water) penetrating well beyond the target depth (15 cm). On the other hand, plant and generally biologically available water is that held in the soil between roughly field capacity (33 kPa) and the wilting point (1500 kPa). From the literature this is about 0.17 cm of water per cm of soil for loamy or clayey soils. (See, Troeh F. R., Hobbs J. A., and Donahue R. L., "Soil and Water Conservation for Productivity and Environmental Protection," Pearson Prentice Hall Pubs., Upper Saddle River, NJ, 2004, p. 403). Using this figure, a depth of 2.55 cm of water would provide water to the target depth (15 cm) without deeper penetration into the CI horizon. This equates to 6.375 liters of solution per plot.

In this study phosphorus, either as phosphate or phosphite, was added at a rate of 120 kg of P per hectare (ha). Scaled down this equates to 3 grams of phosphorous per plot. One ha is 10,000 $m^2$. Each plot is 50 cm by 50 cm, or 0.25 $m^2$. The subsequent calculation then is 120 Kg/10,000 $m^2$=X/0.25 $m^2$; X=3.00 grams of P per plot. (See Table 2).

Treatments: All plots received the same amount of solution. The control plots were treated with distilled water only (6.375 L). The KCl plots treated with distilled water containing the same amount of K as was needed to convert the phosphorous acid ($H_3PO_3$) to dipotassium phosphite ($K_2HPO_3$). The phosphate plots were treated with sufficient dipotassium phosphate ($K_2HPO_4$) to deliver 3 g of P per plot dissolved in the same amount of distilled water as the control plots received and the KCl plots received. The phosphite plots were treated with sufficient dipotassium phosphite ($K_2HPO_3$) to deliver 3 g of P per plot dissolved in the same amount of distilled water as the control plots received, the KCl plots received and the phosphate plots received.

Plot treatments summary. Each plot was 50 cm by 50 cm. A single plot is an experimental unit. Each treatment was replicated three times. Prior to adding solutions to soils, the E.C. and pH of the solutions was checked to be sure those value corresponded approximately to the E.C. and pH of the soil.

TABLE 2

| Plot Treatment: | Added P Ha [1] | Added P Scaled to 0.25 $m^2$ | Added K Scaled to 0.25 $m^2$ |
|---|---|---|---|
| Control | 0 | 0 | 0 |
| KCl | 0 | 0 | 7.774 g |
| $K_2HPO_4$ | 120 Kg | 3 g | 7.774 g |
| $H_3PO_3$ [2] | 120 Kg | 3 g | 7.774 g |

Notes for Table 2:
[1] The plot size of 0.25 $m^2$ occupies a surface area of 2,500 $cm^2$. The target depth of 15 cm times 2,500 $cm^2$ was a volume of 37,500 $cm^3$ or soil. The bulk density of soil was approximately 1.3 grams per $cm^3$. (see, Paster, 1997, "Soil Science and Management," 3rd ed., Delmar Pub.). Using this bulk density, the total dry weight was 48,750 g. The ratio of grams of added P to this weight indicated the P treament was 61.53 ppm (or μg/g or mg/kg).
[2] The phosphorous acid was added as the dipotassium salt. It was converted to the salt by dissolving the acid in 1 liter of distilled water and adding 10.869 grams of KOH (0.1937 moles) to convert the phosphorous acid to dipotassium phosphite.

The year this experiment was performed was unusually dry in terms of total annual precipitation. Dry soils tend to be hydrophobic. Side plots (see FIG. 2) of the same size as the test plots were established to determine what rate of water could be applied to the plots such that there was no runoff from the plots. Adding all of the distilled water (6.375 L) at once resulted in considerable runoff. Opening slots in the soil with a flat tinned garden fork (FTGF) prior to adding the water was not profitable because the slots filled with dry soil. However, using the FTGF to open slots after addition of 1.90 L of water resulted in an array of slots that took up the remaining 4.485 L of distilled water when added slowly.

Although the acids phosphoric ($H_3PO_4$) and phosphorous ($H_3PO_3$) and the potassium salts of these acids are all soluble to very soluble in water (Lide, 1998-1999, Ibid.), it is well known that in soils phosphorus is rapidly chemically immobilized. Phosphorus is most soluble at a soil pH of near 6.5. Below that it combines with aluminum and iron to form almost insoluble complexes. Above 6.5, it combines with calcium to also form nearly insoluble complexes. (See, Troeh and Thompson, "Soils and Soil Fertility," Oxford University Press, 1993).

Twelve range soils in the Laramie Basin of SE Wyoming were analyzed for total and extractable phosphorus. (See, Watson D. M. H., "Vesicular-Arbuscular Mycorrhizae of sagebrush (*Artemisia* Spp) in SE Wyoming," University of Wyoming Library, Laramie, WY, 1987, pp. 148-179). Total phosphorus (Association of Official Agricultural Chemists (AOAC), "Phosphorus first action: Magnesium nitrate method," In: Horwitz, W., "Official Methods of Analysis of the AOAC," Washington, D. C., 1955, p. 25) of these samples averaged 406 mg/kg (standard deviation 291 mg/kg). Extractable phosphorus (see Olson S. R. and Sommers L. E., "Phosphorus soluble in sodium bicarbonate," In: Page A. L., Miller R. H., and Keeney D. R., "Methods of Soil Analysis Agronomy 9," Soil Science Society of America, Madison, WI, 1982, pp. 421-422) averaged 7.1 mg/kg with a standard deviation of 3.7 mg/kg. The saturated paste pH (Salinity Laboratory Staff, "pH reading of a saturated soil paste," In: Richards, L. A., "Diagnosis and Improvement of Saline and Alkali Soils," Agriculture Handbook 60, Washington D. C., U. S. Govt. Printing Office, 1954, p. 102). Of these, samples were alkaline enough (average of pH=7.1 with a standard deviation of 0.52) that most of the total P was in the form of calcium complexes. According to this, less than 2% of the total P in these soils was in a biologically available form.

In conclusion, the soil surface was opened with the FTGF to permit relatively rapid penetration of the treatment solutions into the soil and to allow the phosphorus in the solutions to interact with the soil to depth rather than just with the immediate surface soil. This was done on all the plots. Other means of incorporating the treatment material (such as a plot equivalent of plowing) were not considered because they would have disrupted the native plant roots in the plots. Maintaining an intact native plant root system was crucial to the experiment described in Example 4, below.

The treatment of each plot proceeded by: (1) sprinkling 1.90 liters of the treatment solution on the plot surface uniformly such that there was no runoff from the plot; (2) after 15 minutes, the FTGF was used to create slots in the surface, a line of 12 slots (the FTGF had 4 tines) was created at 2 cm from the NW edge of each plot, a total of 9 such lines of slots were created across the plot at 5 cm intervals for a total of nine lines of 12 penetration and thus 108 slots across each plot, the FTGF was pushed into the soil with moderate foot pressure to 10 cm, before withdrawing the fork, it was oscillated back and forth to create a slot of about 1 cm width; and (3) the remaining treatment solution was then sprinkled uniformly across the plot.

This procedure was also performed on the side plots with water. After 30 minutes the depth to which the water had penetrated was checked. It had penetrated to 10.5 cm. The water probably penetrated further, but it was decided to restrict sampling to the top 10 cm of the plot soils.

Potassium chloride treatment proceeded as follows: each KCl plot received 6.375 liters containing 14.446 grams of KCl in distilled water. This is the same amount of potassium used to convert $H_2PO_3$ to $K_2HPO_3$ (see below).

Application of the potassium salt solution was the same as indicated above for the control plots: (a) 1.90 liters of the solution was applied to a given KCl treated plot uniformly across the plot at a rate such that the solution penetrated without running off the plot; (b) the plot was penetrated uniformly as described above with the FTGF; and (c) the remaining solution, 4.485 liters, was applied uniformly across the plot. The three KCl plots were all treated in this manner.

Dipotassium phosphate treatment was performed as follows: each $K_2HPO_4$ plot received 6.375 liters containing 16.870 grams of $K_2HPO_4$ in distilled water. This level of potassium was equivalent to the amount added to the KCl treatments as well as the dibasic potassium phosphite treatments (below).

Application of the dibasic potassium phosphate solution was the same as indicated above for the control plots, as follows: (a) 1.90 liters of the solution was applied to a given $K_2HPO_4$ treated plot uniformly across the plot at a rate such that the solution penetrated without running off the plot; (b) the plot was penetrated uniformly as described above with the FTGF; and (c) the remaining solution, 4.485 liters, was applied uniformly across the plot. The three $K_2HPO_4$ plots were all treated in this manner.

Dipotassium phosphite treatment was performed as follows: phosphorous acid was converted to the dipotassium salt prior to mixing with distilled water. Reagent grade phosphorous acid (8.104 grams, 0.0969 moles) was dissolved in 1 liter of distilled water. Potassium hydroxide (10.869 grams, 0.1937 moles) was added to the solution. The acid reacted with the base as in the following reaction to create the dipotassium phosphite:

$$H_3PO_3 + 2KOH \rightarrow K_2HPO_3 + 2H_2O$$

Distilled water was added to the solution to bring the volume up to 6.375 liters. The treatment then proceeded as with the other plots. That is: (a) 1.90 liters of the solution was applied to a given $K_2HPO_3$ treated plot uniformly across the plot at a rate such that the solution penetrated without running off the plot; (b) the plot was penetrated uniformly as described above with the FTGF; and (c) the remaining solution, 4.485 liters, was applied uniformly across the plot. The three $K_2HPO_4$ plots were all treated in this manner.

Prior to the application of treatments, three soil samples were taken from between the rows of plots. (See, FIG. 2, at soil surface sampling sites, marked 'X' on the diagram). Each of these samples was taken to a depth of 5 cm and air dried. Each sample was sieved through a 2 mm sieve to separate active soil from inactive soil, i.e., large particles of soil that may interfere with test equipment and preclude accurate readings. From the resulting material 10.0 g was weighed into a plastic cup and 20 ml of distilled water added. The mixtures were stirred intermittently for 30 minutes and allowed to settle for one hour. Electrical conductivity (a measure of dissolved salt) and pH of the supernatant (the liquid above the settled soil) was made using a handheld pH/EC meter (Oakton EC Tester 11, by Eutech Instruments Pte. Ltd., Paisley, UK). Electrical conductivity averaged 177 µS/cm (or 0.177 mS/m) and pH 7.91. These ECs and pHs are in the range that this soil is neither saline or sodic. (See, Gavlak R., Horneck D., and Miller R. O., "Soil Analytical Methods," Soil pH (1:2) and Soil EC (1:2), In: "Soil, Plant and Water Reference Methods for the Western Region," 3$^{rd}$ Ed., 2005, pp 37, 47, and 49). As solutions were added to the plots, EC and pH of those solutions were recorded. The EC measurements of the solutions were all equivalent to the surface soil sample EC. pH measurement were mostly within 0.1 to 0.2 pH units from the average of the soil surface samples. The few that deviated were adjusted with dilute hydrochloric acid or dilute potassium hydroxide.

All plots were treated, as above, June 15 and 16. The study continued from these dates until October 15 for a total of 121 days-with periodic sampling of plants and soil. Temperatures and precipitation plus supplemental water additions were sufficient to maintain plant viability (Table 3). After October 15 plant growth had stopped largely due to low temperatures (Table 3).

TABLE 3

| | Temperature, ° C. | | Precipitation, cm | | | |
|---|---|---|---|---|---|---|
| | | | | | Days | |
| | Mean | Mean | Total Melted | Days with | Added | Amt Added |
| Month | High | Low | Precip | Precip | Water | per day |
| June | 22.1 | 6.4 | 0.36 | 4 | 1 | 1.38 |
| July | 28.4 | 9.6 | 2.64 | 12 | 0 | 0 |
| August | 25.5 | 8.2 | 2.51 | 10 | 17 | 0.24 |
| September | 21 | 4 | 2.16 | 10 | 12 | 0.24 |
| October | 12 | −2 | 3.1 | 5 | 0 | 0 |

Temperatures were recorded at the NOAA weather station at the Laramie Regional Airport, located 11 km west of the test site at 2,216.5 m elevation (datum mean sea level) at Lat/Long of 41.32° N and 105.67° W. Precipitation recorded at the plot site at 2,277 meters elevation and Lat/Long of 41.32° N and 105.54° W. On June 27, plots were watered (1.38 cm depth) between 5:30 and 7:15 hours. Water supplement during August amounted to 4.08 cm added in 0.24 cm increments. Water supplement during September amounted to 2.88 cm added in 0.24 cm increments. Most of the October precipitation was snow. All amounts shown are as liquid equivalents, i.e., melted precipitation.

Note on added water: Added water was Laramie Municipal water. The water used in this experiment was a mixture from three different wells that serve the area where this experiment was conducted. Water analyses were conducted by the Wyoming Department of Agriculture, Analytical Services Laboratory (EPA Methods: 300.0 for nitrite, 200.8 for metals, and 200.7 for anions, see EPA 300.0, EPA 200.8, EPA 200.7, Environmental Protection Agency, U.S., available at epa.gov). Analysis showed pH was 7.966 (standard deviation of 0.06) and EC 364 (23) µS/cm. Ca, Mg, K, and Na were, respectively, 49 (standard deviation of 2), 16 (0.7), 0.8 (0.1), and 3 (0.7) ppm. Bicarbonate, carbonate, nitrate, nitrite, and sulfate were, respectively, 186 (7), 2 (0), 2 (0.2), 0.2 (0), and 9 (2) mg/L.

The first soil and root samples were taken on June 30 (14 days from start), the second on Aug. 16, 2017 (61 days from start), and the third set on October 15 (121 days). All samples were air dried and stored. Subsamples of the first set of soils were sent August 3 for chemical and physical analysis. (Pace Analytical, Sheridan, WY, US).

Each sample was an approximately rectangular prism of soil to 10 cm below the surface and 7.5 to 8.5 cm square at the surface. This resulted in 700 to 1000 grams of soil per sample. Samples were air dried (100 hours at 20° C.) and passed through a 2 mm sieve. Coarse material (>2 mm) was weighed and discarded.

Roots and plant tops were removed, identified, and roots were stored by plant species. Plant tops were discarded. Roots were placed in 7 ml screw capped vials. FAA solution was added to preserve the samples (FAA solution for 2 liters:1 liter ethanol (95% denatured), glacial acetic acid 100 ml, formaldehyde 200 ml, and distilled water 700 ml). Further processing of roots is discussed in Example 5 below.

Soil analyses (Table 4) were performed using standard soil methodologies: extractable (plant available) phosphate and total phosphorus (Olsen, S. R. and L. E Sommers, 1982, "Phosphorus," In: Page A. L., Miller R. H., and Keeney D. R., "Methods of Soil Analysis, Agronomy No. 9," American Society of Agronomy, Madison, WI, 1982, pp. 403-430); total and nitrate nitrogen (Bremner, J. M. and Mulvaney C. S., "Nitrogen—Total," In: Page A. L., Miller R. H., and Keeney D. R., "Methods of Soil Analysis, Agronomy No. 9," American Society of Agronomy, Madison, WI, 1982, pp. 595-624); total and total organic carbon (Skjemstad et al., "Total and Organic Carbon," In: Carter M. R. and Gregorich E. G., "Soil Sampling and Methods of Analysis," CRC Press, Boca Raton, FL, 2008) and pH and Electrical conductivity (Gavlak R., Horneck D. and Miller R. O., Ibid. 2005).

Table 4 provides data concerning the soil analysis of the August 3 samples from the plot study at the field site. Abbreviations—TKN: Total Kjeldahl Nitrogen, TOC: Total Organic Carbon, pH made on 2:1 $H_2Od$ (distilled water) to soil, EC: electrical conductivity taken on 2:1 $H_2Od$ to soil, (H+): hydrogen ion activity, µS: micro Siemans, SD: Standard Deviation. Sample ID shows treatment and Plot number (see FIG. 2).

TABLE 4

| Sample ID | Plot No. | Extracted P (ppm) | Total P (mg/kg) | Nitrate (as N) (ppm) | Nitrogen TKN (%) | Total Carbon (%) | TOC (%) | pH − log (H$^+$) | EC (µS/cm) |
|---|---|---|---|---|---|---|---|---|---|
| Control | 1 | 82 | 1590 | 3.2 | 0.26 | 2.2 | 1.8 | 7.51 | 320 |
| Control | 6 | 33 | 835 | 2.9 | 0.18 | 1.7 | 1.4 | 7.77 | 340 |
| Control | 8 | 53 | 1110 | 0.1 | 0.24 | 2 | 1.6 | 7.72 | 320 |
| Mean | | 56 | 1178.33 | 2.07 | 0.23 | 1.97 | 1.60 | 7.67 | 326.67 |
| SD | | 24.64 | 382.11 | 1.71 | 0.04 | 0.25 | 0.20 | 0.14 | 11.55 |
| KCl | 2 | 106 | 2550 | 2.3 | 0.23 | 2.1 | 1.8 | 7.53 | 530 |
| KCl | 4 | 51 | 938 | 4.5 | 0.18 | 1.7 | 1.3 | 7.74 | 490 |
| KCl | 12 | 18 | 1050 | 5.8 | 0.17 | 1.8 | 1.5 | 7.74 | 440 |
| Mean | | 58.33 | 1512.67 | 4.20 | 0.19 | 1.87 | 1.53 | 7.67 | 486.67 |
| SD | | 44.46 | 900.10 | 1.77 | 0.03 | 0.21 | 0.25 | 0.12 | 45.09 |
| PO$_4$ | 3 | 84 | 1200 | 4 | 0.19 | 2.1 | 1.7 | 7.81 | 390 |
| PO$_4$ | 7 | 91 | 972 | 5.9 | 0.21 | 1.7 | 1.3 | 7.8 | 330 |

TABLE 4-continued

| Sample ID | Plot No. | Extracted P (ppm) | Total P (mg/kg) | Nitrate (as N) (ppm) | Nitrogen TKN (%) | Total Carbon (%) | TOC (%) | pH – log (H+) | EC (µS/cm) |
|---|---|---|---|---|---|---|---|---|---|
| PO$_4$ | 11 | 199 | 2460 | 4.8 | 0.25 | 2.3 | 2 | 7.37 | 340 |
| Mean | | 124.67 | 1544.00 | 4.90 | 0.22 | 2.03 | 1.67 | 7.66 | 353.33 |
| SD | | 64.47 | 801.43 | 0.95 | 0.03 | 0.31 | 0.35 | 0.25 | 32.15 |
| PO$_3$ | 5 | 158 | 2300 | 6.3 | 0.22 | 2 | 1.7 | 7.59 | 450 |
| PO$_3$ | 9 | 83 | 814 | 2.8 | 0.18 | 1.8 | 1.4 | 7.84 | 410 |
| PO$_3$ | 10 | 167 | 2050 | 8 | 0.2 | 2.1 | 1.7 | 7.58 | 450 |
| Mean | | 136.00 | 1721.33 | 5.70 | 0.20 | 1.97 | 1.60 | 7.67 | 436.67 |
| SD | | 46.12 | 795.65 | 2.65 | 0.02 | 0.15 | 0.17 | 0.15 | 23.09 |

The main feature of the soil analysis in Table 4 is phosphorus. Those plots not receiving any added P (controls and KCl treatment) showed essentially background levels of extractable P, assumed to be phosphate. Plots receiving added P showed 70 to 80 ppm (µg/gram) of increased extractable P over background levels. Target treatment of these plots was to increase the extractable P to 61 ppm above background levels. The soil analysis shows this was accomplished, and exceeded. The explanation for this is that treatment solutions did not penetrate completely to the 15 cm depth, but instead only penetrated to a depth of 10.5 cm. More importantly, statistical comparison of mean values (T Test) showed highly significant differences in mean values between all P treated plot analyses and all untreated plot analyses (alpha=0.007). This argument is reflected in the comparison of means between the Control versus Phosphate treatments as well as the Control versus Phosphite treatments (alphas of 0.08 and 0.03, respectively). It is further displayed by the KCl versus phosphate treatments as well as the KCl versus phosphite treatments (alphas of 0.11 and 0.05, respectively). The key conclusion from these data is that the phosphate versus phosphite mean values were not significantly different, providing evidence that these two measurements were statistically the same.

Note concerning statistical significance: alphas of less than 0.01 are herein defined as highly significant. Alphas of less than 0.05 are defined as significant. Some alphas are near 0.10 and herein are described as near significant.

Total phosphorus showed some differences between treatments, but none of these except the control versus phosphite showed a significance difference (alpha of 0.017). All treatments involving P should have more total phosphorus than those where phosphorus was not added. (See, "Classic Literature Summary," Mattingly F. E. G. and Talibuden O., "Progress in the chemistry of fertilizer and soil phosphorus," In: Grayson and Griffith, "Topics in Phosphorus Chemistry," 4:157-290, 1967; see also, Troeh F. R. and Thompson L. M., 1993, and Sever, M., "Managing Phosphorus and Potassium is Key in Conservation Tillage Systems," Crops and Soils, 54(2):14-17, 2021). Inspection of this data (Table 4) shows that although the mean total phosphorus of the plots receiving no added P was 1346 mg/kg and the mean of plots receiving added P was 1633 mg/kg, there was so much variability that this mostly obscures any treatment statistical significance for total P.

The mean comparisons for nitrate showed a significant difference for the control versus phosphate (alpha of 0.03) and near significant differences for the control versus KCl and the control versus phosphate (0.10 and 0.06, respectively). An explanation for this is addition of exogenous P can increase biological activity such that organic nitrogen from the Total Kjedahl Nitrogen (TKN) pool as well as the organic pool may be mineralized (that is modified from an organic form to an inorganic form). Even though there are changes in the nitrate pool, these changes are only in the order of 2 to 5 ppm as nitrate N. Several studies in similar rangelands, especially semiarid cool rangeland, show this is not enough change in plant species composition to impact below ground processes. (See, Rauzi F., "High Ratges of Nitrogen Change Composition of Short Grass Rangeland in Southeastern Wyoming," *J. Range Management*, 31:366-370, 1978; see also, Peterson G. A., Williams S. E., and L. E. Moser, "Inorganic Fertilizer use and its Effects on Semiarid and Arid Region Soils," In: Skujins J., "Semiarid Lands and Deserts," New York, NY, Marcel Dekker, Inc., 1991, pp. 543-580). These changes have not resulted in significant TKN and carbon (total or total organic) changes. These measures are in percentages, TKN being approximately 0.21% or 2,100 ppm. Changes of a few ppm in the TKN would not be expected to show up as a significant change in this comparatively large pool of nitrogen.

The other series of mean comparisons is electrical conductivity (EC). Here almost all comparison showed significant difference in means between controls and treatments, between KCl and phosphorus treatments as well as differences between the phosphate and phosphite treatments. In general, it would be expected that addition of salts of any sort would increase the EC over controls. In any event, these increases are modest and do not result in EC values that would come close to classification of these soils as saline. (See, Gavlak R., Horneck D., and Miller R. O., Ibid. 2005). The pH values also are low enough that these soils would not be classified as sodic (at pH of 8.2 sodium problems are slight, at 8.4 sensitive plants may be impacted. (See, Carlstrom M. G., Amendola F. A., Shay D. A., and Dollhopf D. J., Chapter 5, "Sodium," In: Williams D. and Schuman G. E., "Reclaiming Mine Soils and Overburden in the Western United States," Ankeny, IA, Soil Cons. Soc. of America, 1987, pp. 75-108).

Of note however is the EC difference between the phosphate and the phosphite treatments (alpha of 0.01). This suggests that the dipotassium salt of phosphite is more soluble than the dipotassium salt of phosphate, although published information suggests they are equally soluble. (Lide 1998-1999, Ibid.).

The overall importance of these findings is that analysis of phosphorus as extractable phosphorus does not distinguish between phosphate and phosphite forms. The standard analysis method for extractable P (Olsen S. R and Sommers L. E., Ibid.) assumes that extractable (plant available P) soil P exists as phosphate. These data suggest that extractable P may also contain phosphites, and that these will be indistinguishable from phosphates. This argument holds also for total phosphorus. Total P is determined by strong acid digest and final determination by ICP (Inductively coupled plasma). This will not distinguish between any different forms of phosphorus be they different valences, organic, inorganic or elemental.

Example 4: Arbuscular Mycorrhizae in Roots and Soil, A Field Study A major focus of the field study described above (in Example 3) was investigation of soil analysis for phosphorous and specifically for total phosphorus, phosphate phosphorus, and phosphite phosphorus. The experimental design in Example 3 was used in this example to examine the influence of phosphate and phosphite on AM fungi. A general hypothesis to this end is that phosphite will have a positive impact on AM fungi. This would be manifest as an increase in the infection levels of roots of plant susceptible to AM fungi infection as well as an increase in the AMF spores in soils treated with phosphite. Null hypotheses in this context would be that there would be no impact of phosphite on AMF and that this would be manifest as no increase in infection levels or increase in spore numbers.

The treatment scenario described in this example was established mainly to focus on the impact of phosphite on AM fungi. A phosphate treatment was also included to ensure that any impact of phosphite on AM fungi was not just a general phosphorus effect. However, the general consensus from fairly early work with AM fungi is that biologically available phosphate in soils tended to inhibit AM fungal activity. (See, Cooper K. M., "Physiology of VA Mycorrhizal Associations," In: Powell and Bagyaraj, VA, "Mycorrhizae," CRC Press, Boca Raton, FL, 1984, pp. 155-186). However, this generalization has been shown as inaccurate. Numerous researchers have shown mycorrhizal activity is not inhibited by high available soil phosphate levels. (See, Rhodes et al., *Soil Biol. Biochemistry*, 10:361-364, 1978; and Li et al., *New Phytol.*, 119:397-404, 1991). Although soil phosphorus uptake and translocation to host plants is one of the principle and well recognized functions of VAM fungi (Luginbuehl L. H. and Oldroyd F. E. D., *Current Biology*, 27:R952-R963, 2017), increased bioavailable soil phosphorus does not necessarily enhance or depress the activity of the fungus on the host plant and thus in the soil.

"Increased activity" of AMF is recognized as a detectable increase in the infection level of host plant roots and increased levels of spores in the soil. Stahl P. D. and Williams S. E. ("Oil Shale Process Water Affects Activity of Vesicular-Arbuscular Fungi and Rhizobium 4 years after Application to Soil," *Soil Biol. Biochemistry*, 4:451-455, 1986) showed that toxic substances (a waste oil shale retort water) applied to soils resulted in depressed activity of these fungi in terms of decreased infection rates of host plants as well as depressed spore production by the fungi. Further, in disturbed land restoration maintenance of mycorrhizal inoculum density and mycorrhizal potential (potential to colonize root systems) are essential to remediation. (See, Miller R. M and Jastrow J. D., "The application of VA mycorrhizae to ecosystem restoration and reclamation," In: Allen M. F., "Mycorrhizal Functioning," Chapman & Hall, New York, NY, 1992, pp 438-467).

The field experiment reported in this example was conducted during June through October. Plots were established during early June and treated on the $15^{th}$ and $16^{th}$ day (as in Example 3 above). The first soil and root sampling was performed 14 days later (t=14). The second set of samples were taken 47 days later (t=61), and the third set 60 days later (t=121 days). Sample size and depth was as detailed above in Example 3.

Plants in the test plots include several native plants and some exotics. The natives were western wheatgrass (*Pascopyron smithii* also listed as *Agropyron smithii*), gramma grass (*Boutelua gracilis*), desert madwort (*Alyssum desitorum*), and scarlet globe mallow (*Spheralcea connea*). There were also several exotics in the plots at relatively low density: Kochia (*Kochia scoparia*) and downy brome or cheatgrass (*Bromus tectorum*). The two native grasses are in the Poaceae family. Madwort is a mustard (*Brassicaceae*) and the globe mallow in the Malvaceae family. The two exotics are in the Amarathaceae and the Poaceae, respectively. Also present on a few of the plots was yellow sweet clover, a native in the family Fabaceae (*Melilotus officinalis*). The wheatgrass, gramma grass, mallow and sweet clover are all listed as AM mycorrhizal. The cheatgrass is listed as facultatively AM mycorrhizal. The madwort and kochia are non-mycorrhizal. (See, Wang B. and Qui Y.-L., *Mycorrhiza*, 16:299-363, 2006).

Analyses of infections were performed by examining roots of wheatgrass (*Pascopyron smithii*). This plant was the dominant plant in all of the plots and is known to be commonly infected with AM fungi. (See, Loree M. A. J. and Williams S. E., *New Phytologist*, 106:735-744, 1987; and Wang B. and Qui Y.-L. 2006, Ibid.). During sampling of soils using the methodology outlined in Example 3, above, root of target plants were removed and separated by plant species, each sample being labeled and preserved in FAA solution until being further processed.

Staining of the roots was achieved according to published procedures (see, Phillips J. M. and Hayman D. S., *Trans. Brit. Mycological Soc.*, 55:158-160, 1970) except that cotton blue lactophenol was substituted with lactic acid glycerol with trypan blue since lactophenol is toxic. The procedure used for staining was as follows:

A) Remove roots from FAA Solutions. Cut into 1 cm lengths. Place in test tube, push roots to the bottom of the test tube.
B) Cover roots with 10% KOH (10 grams of reagent grade KOH in enough distilled water to 100 ml). Let stand overnight, about 10 hours.
C) Simmer at 90° C. for one hour in a water bath (container with water and test tubes with roots over a heat source).
D) Rinse in tap water.
E) Rinse five minutes in 0.1 N HCl (3.65 gram equivalents of HCl in 1000 ml total volume with distilled water).
F) Rinse in tap water.
G) Simmer at 90° C. one hour (in water bath) in Trypan blue Lactic Acid Glycerol (distilled water, 100 ml; lactic acid (reagent grade 85 to 88%) 100 ml; glycerin (reagent grade 85% also listed as glycerol), 200 ml; trypan blue, 0.1 grams (60% dye content).
H) Rinse in tap water.
I) Place in clear lactic acid glycerol (same formulation as above except without the Trypan blue) if destaining is necessary. Samples can be simmered at 90° C. (one hour in water bath) or left at room temperature for at least 72 hours or longer.
J) Mount on standard glass slide (2.5 cm by 7.6 cm) in lactic acid glycerol. Cover slip (2.3 cm by 4.8 cm) used.

Mounting of roots and observation of roots was made initially at a cursory level using a dissecting microscope (United Scope, Irvine, CA, US; 3.5× to 90× stereo-microscope). Comprehensive microscopic analysis was conducted using a compound, light microscope (Leica Microsystems, Buffalo Grove, IL, US; DMLB Research Microscope: bright field and DIC applications, with 10×/22 mm eyepieces, N Plan 10×, 20×, and 40× objectives and mechanical stage with slide holder).

The cursory evaluation of root samples included examination of scarlet globe mallow, kochia, desert madwort, and western wheatgrass. As expected from previously published work (Wang B. and Qui Y.-L. 2006. Ibid.), the kochia and madwort were not infected with AMF. The globe mallow and wheatgrass (also previously reported) were infected. Globe mallow, however, is very deeply rooted and the proper sized roots were not usually present in the top 15 cm of the test plots, which were the focus of this investigation. Roots of western wheatgrass were abundant and principally located in the top 15 cm of the test plots.

Proper sized roots for viewing optimum AMF infections are generally those that are the finest level of branching of a plant root system. The diameter of these finest level of branching varies according to plant groupings (genus level and sometimes at the family level of taxonomy). For plants in the family Poaceae, the grasses, these may be roots of less than 0.1 mm in diameter. The roots of western wheatgrass examined in this study ranged up to 1 mm in diameter. In any event, the infection occurs only in the epidermal cells of the root as well as in the cortex. The infection does not penetrate into the vascular cylinder. (See, Bonfante-Fasolo P., "Anatomy and morphology of VA mycorrhizae," In: Powell C. L and Bagaraj D. J., VA, "VA Mycorrhiza," CRC Press, Boca Raton, FL, 1984, p. 5034). Infections in the vascular cylinder and the meristem regions of the root are indications of pathogenic fungi and not the symbiotic AM fungi.

The critical diagnostic characteristic of AM fungal infection or plant root association is the arbuscule. Other diagnostic characteristics that are often more plant or fungus specific are the presence of vesicles, peletons (coiled hyphae in single cells), appressoria (infection pegs on exterior of epidermal cells), spores inside the roots and variable hyphal characteristic. (See, Bonfante-Fasolo, P., 1984, Ibid.). The hyphae vary widely in diameter from one species to another are intercellular, often of variable diameter even within a species and coenocytic (aseptate).

An estimate of the degree of infection of western wheatgrass was made by making microscopic scans of each slide such that 40 root segments were evaluated. The evaluation was performed using the 20× objective, e.g., 200× total magnification—eyepieces were 10× multiplied by the objective magnification. The diameter of the complete field of view at 200× was 1100 µM (or 1.10 mm). Thus 40 views constituted viewing 44 mm of root.

A root segment of 1.10 mm was considered to be infected if any of the diagnostic features of AM fungal infection was observed in that segment. From the total of 40 observations a percentage of infection was derived by multiplying the ratio of infected segments observed over total segments observed by 100. Also, for each slide of roots observed, a general qualitative assessment was made of the intensity of infection across an entire slide. Intensities were given a score of +, ++, +++, or ++++, where these corresponded respectively to low infection (one to ten diagnostic features per segment observed), modest infection ten to 30 diagnostic features per segment), high infection (30 to 60 diagnostic features), and very high (more than 60 features).

Fungi other than AMF were observed on most roots. These were not included in the estimates but their presence was recorded. Most of these fungi were identified because their hyphae were regularly septate, i.e., not coenocytic. Others were the classic problem fungi that to some degree resemble AMF. These are of the *Olpidium* genus, an obscure fungus in the Cytridiales, and *Polymixa graminis*, a fungus common in many grasses including the genus *Pascopyron* (synonym *Agropyron*). (See, Gerdemann. J. W., "Occurrence of *Polymyxa graminis* in red clover roots," *Plant Disease Reporter*, 39:859, 1955).

AMF spores were evaluated in soil samples from which plant roots including plant roots of western wheatgrass had existed and had been removed. Evaluations were performed on the T=0 and the T=47 samples. These evaluations generally entailed mixing the sample with water, centrifugation, and decanting water. This step was performed to remove light organic matter and other light materials, e.g., leaf fragments. This was followed by mixing the soil with a solution of sodium hexametaphosphate (2%) in 2 M sucrose. Centrifugation results in the spores floating on the sucrose solution or suspended in it. The sucrose solution plus spores is decanted into a separatory funnel. The suspension was allowed to exit the funnel one drop at a time. The spores adhere to the inside of the funnel and once all liquid has exited the funnel the spores are washed into a petri-dish and counted under a dissecting microscope.

The specific protocol for spore extraction was as follows:
A) Weigh 5 g of air dried soil into a 20 ml centrifuge tube. For a complete sample this is replicated four times.
B) Fill each tube with water to ~1.5 cm of the top. Stir to suspend organic matter and other light debris. Let all tubes stand for 10 minutes.
C) Centrifuge at 2000 rpm (475.2×g) for 10 minutes. Be sure tubes are placed across from each other in the centrifuge and are within 0.1 g of the same weight.
D) Pour off and discard supernatant while stirring surface and rotating tube.
E) If much organic matter and other light material remains, repeat steps B through D.
F) Add sucrose/sodium hexametaphosphate solution (2 molar sucrose containing 2% hexametaphosphate: 684.6 g of sucrose (store grade is adequate) and 20 g of sodium hexametaphosphate in one liter of solution using distilled water) to centrifuge tubes to ~1.5 cm of top. Stir vigorously for three minutes to suspend. Let tubes stand 10 minutes.
G) Centrifuge for 10 minutes at 2000 rpm (475.2×g).
H) Decant and save supernatant. Discard solids in tube bottoms.
I) Add collected supernatants from the four tubes to a separatory funnel. Let stand for 10 minutes.
J) Set funnel to drip (one drop at a time). Discard liquid passing through funnel.
K) Wash materials sticking to the funnel wall into a petri dish using a minimum amount of water.
L) View and count spores under dissecting scope.

Viewing and counting spores was performed using the stereoscopic dissection microscope scope described above. Calculations of the number of spores per 100 g of soil was performed according to the procedures detailed by Watson, 1987. Ibid. (See also, Allen et al., *Mycologia*, 71:666-671, 1979). The modification in this example from the published protocol is that the bottom of the petri dish was fitted with graph paper showing 1 $cm^2$ sectors. Ten sectors were randomly selected from the total 62.21 $cm^2$ area of the petri dish bottom. Spores were randomly distributed throughout the petri dish bottom using a narrow stream of water. Spores in each 1 $cm^2$ sector were counted and the ten sectors totaled. The sum was multiplied by 31.05 (6.21×5; to get the total number of spores in the petri dish, the total of the ten 1 $cm^2$ sectors was multiplied by 6.21, the factor to bring the spore estimate to the total for the entire petri dish; the spore number in the petri dish represent the total in 20 grams of soil. Needed is the number for 100 grams, the standard manner to report spore numbers and thus the total number of spores in the petri dish multiplied by 5).

Only cursory attempts were made to taxonomically identify the species of mycorrhizae present in the examined samples. The hyphal attachment (subtending hyphae) of the spore is distinctive (bulbous, funneliform, or simple), the spore walls are thick often with distinctive layers, spores may be colored (with greenish yellow, honey colored, white, dark brown, tan, or very light brown luster) and often large (average of 100 µm, some are smaller down to 10 µm some much larger over 250 µm). Spores were counted under the dissecting scope and when necessary spores were place under the compound microscope to determine specific structures.

The results of this field experiment showed that infections of the roots of the target plant, western wheatgrass, were normal as were the spore counts from the associated soil. (See, Table 5).

For the data provided in Table 5, spore counts were performed across two sampling times and infection levels across three sampling times. Correlations ('r') were established between spore counts and infection levels, of which none of these were significant at any level. Comparison of means (T Tests) for spores from treatment to treatment within a sample time (t=0 or t=47) were not significantly different at any level. The test plant examined for AMF infections was western wheatgrass (*Pascopyron smithii*) and spores were those from soil around the root system of this plant. Means followed by the same capital letter within a sampling time (columns) are not significantly different at an alpha of less than or equal to 0.05. For chemical species $PO_4$ and $PO_3$, means (t=47, infection), the T Test alpha is 0.0015, highly significant. Means followed by the same small letter within a treatment within either spores or infection (rows) are not significantly different at an alpha of less than or equal to 0.05.

TABLE 5

| Treatment Plot ID n = 3 for Each | Total Spores t = 0 days Per 100 g soil | Total Spores t = 47 days | AM Infection t = 0 days | AM Infection t = 47 days Per forty 1.1 mm root segments | AM Infection t = 97 days |
|---|---|---|---|---|---|
| Control |  |  |  |  |  |
| Mean | 5267Aa | 12401Aa | 33Aa | 29Aa | 40Ab |
| Stan Dev | 4745 | 4999 | 5 | 5 | 0 |
| CV, % | 90 | 40.2 | 14.2 | 16.8 | 0 |
| KCl |  |  |  |  |  |
| Mean | 6398Aa | 14806Ab | 31Aa | 34Aab | 36BCabc |
| Stan Dev | 2519 | 1366 | 2 | 3 | 2 |
| CV, % | 39.3 | 9.2 | 7.4 | 7.8 | 4.2 |
| $PO_4$ |  |  |  |  |  |
| Mean | 4998Aa | 12960Ab | 31Aa | 38.7Bbc | 38ACc |
| Stan Dev | 2802 | 2751 | 3 | 1 | 2 |
| CV, % | 56 | 21.2 | 8.5 | 3 | 5.3 |
| $PO_3$ |  |  |  |  |  |
| Mean | 6429Aa | 17896Ab | 32Aa | 31Aab | 39ACc |
| Stan Dev | 1700 | 7822 | 4 | 2 | 2 |
| CV, % | 26.4 | 43.7 | 12 | 5.6 | 4.4 |

Spore numbers per 100 grams of soil generally increased significantly from the first sampling to the second (from t=0 days to t=47 days). Treatments of the plots did not impact spore numbers at t=0, but there was a significant increase in spore numbers from the control in the KCl treatment, the phosphate treatment and the phosphite treatment in the second, t=47, sampling. This suggests that even an increase in the added nutrient potassium as well as the two phosphorus types had an impact on spore populations in the soils (Table 5).

Root infection levels among the various treatments were not statistically different at the first sampling (t=0), but at the second sampling the phosphate treated plots showed a significant increase over the control, the KCl and the phosphite treated plots. This suggests that at least in this study, the added phosphate increased the level of AMF infection in the wheatgrass roots, probably due to the added phosphate increased root proliferation and overall nutrition of the target plant. That the same affect was not seen in the phosphite treated plants (bold entries in Table 5), requires further explanation (see below).

In the third sampling time (t=97 days) infection levels basically were the same across all treatments (Table 5). The KCl treated plot exhibited a small depression in infection levels compared to the control and phosphorus treated plants, but the phosphite treated plants had returned to the infection levels of the other treatments (Table 5).

That the plants in the phosphite treated plots at T=47 days had infection levels statistically indistinguishable from the controls and the KCl treatment, but highly statically significant from the infection levels of the plants in the phosphate treated plots (alpha of 0.0015), is contrary to published central concepts about AM fungi. The AMF infection scenario coupled with the high spore numbers in the phosphite treatment at the same sampling point in time suggests the AM fungi in the soil at this point were still biologically active and their population expanding without increasing infection in the target plant. Although the spore population mean values between all treatments were not statistically significantly different at t=47, e.g., a T test of the mean of all the treatments except the phosphite treatment compared to the mean of just the phosphite treatment gives an alpha of 0.0811, which is tending towards significance, the actual mean of the population of spores in the phosphite treatment was 3,000 to 5,000 more than in any other treatment (the average of all spore populations across controls, KCl, and phosphate treatment was 13,389 per 100 grams of soil, whereas the average of just the phosphite treated plots was 17,896).

The results of this example plus results from Examples 2 and 3 suggest that AM fungi are capable of growth without the influence of host plants. Host plants can provide the AM fungi with nutrients especially metabolically active carbon probably in the form of sugars or similar. These sugars also provide an energy source for the fungi assuming that AMF have active electron transport mechanisms where ATP can be generated from oxidation of the sugar derivatives.

Example 2 provides references and information supportive of a phosphorus cycle based on oxidation and reduction. Such a cycle is not widely recognized and especially that much of the cycle is dependent on microbial transformations of phosphorus. Example 3 saliently shows that analysis of extractable soil P does not distinguish between phosphate and phosphite P. Example 4 (this example) provides information suggesting that AM fungi are involved in this cycle. AM fungi are highly involved in movement of phosphorus from often insoluble forms in the soil to plants that host the fungus. Given the role that AM fungi have in making phosphorus bioavailable, it seems possible that AM fungi would have a role in a phosphorus cycle based on oxidation and reduction of phosphorus. In Example 4, AM fungi are shown when in the presence of soil phosphite to resist infection of the host plant (western wheatgrass). Simultaneously when in the presence of phosphate infection levels of the host plant are significantly higher. Spore numbers of the AM fungi when in the presence of phosphite remain high as they do when in the presence of phosphate. This is evidence that the fungi are still active in both treatments, but that the AM fungi do not infect (or resist infecting) the host plant when soil phosphite is present. A preliminary conclusion is that the fungus does not need association with the plant to maintain its biological activity when soil phosphite is present, implying a free-living growth phase of this fungus. For this to happen, the AM fungi still need a carbon source and an energy source. The contention here is that oxidation of phosphite to phosphate by the fungus or by a helper organism (bacterial) intimately associated with the fungus provides the energy source. The carbon source is assumed to come from organic materials in the soil.

The salient question that comes from this is: can AM fungi derive sufficient energy from the oxidation of reduced phosphate compounds, such as phosphite to grow and reproduce without contact with plants? Of course, the question also raised is from where will the AM fungi secure carbon? Results of an experiment to test the "free-living hypothesis" and examine the possible use of phosphite as an energy source and simultaneously, but less precisely, identify a carbon source for these fungi, is examined in the following Example 5.

Example 5: Testing the "Free Living" Hypothesis For AMF

The following example is a pot experiment (pots with soil) to test more fully and directly the capacity of phosphite to stimulate the growth of AM fungi. For this purpose, a soil sample from below Sheep Mountain west of Laramie, WY, US, (50 km) was acquired. The purpose of this example is to determine whether AM fungi have the capacity to survive and reproduce separate from live host plants or to live free of association with live plants.

This Example is an un-replicated study to examine whether $PO_3^{-3}$ (phosphite) impacts spore production and infection rate of AM fungi. The fungi were a mixed inoculum source from the University of West Virginia (UWV). UWV holds and maintains the International Culture Collection of (Vesicular) Arbuscular Mycorrhizal Fungi (INVAM). The plant used was yellow blossom sweet clover (Melilotus officinalis). All pots were inoculated, but only half were planted. Each Experimental unit was a 20 cm pot. Substrate for the units were a soil, sand, and inoculum mixture.

The soil obtained from below Sheep Mountain had a pH of 7.3 and was dark in color, and about 4% soil organic matter.

The test plant examined in the field study (Example 4) was western wheatgrass (Pascopyron smithii, also known as Agropyron smithii), a plant reported as AM mycorrhizal (Wang B. and Qui Y.-L., 2006. Ibid.; Loree M. A. J. and Williams S. E., 1987. Ibid.). This plant is reported to be facultatively mycorrhizal (Allen, E. B., 1984, "VA Mycorrhizae and Colonizing Annuals: Implications for Growth, Competition and Succession," In: Williams S. E. and Allen M. F., "VA Mycorrhzae and Reclamation of Arid and Semi-arid Lands," Laramie, WY, Univ. Wyo. Agric. Expt. Stn. Report SA1261, pp. 42-52). Although usually mycorrhizal, in some environments it is not. For this example, it was decided to use a plant that is well recognized as obligatively mycorrhizal. One that has been used extensively is yellow sweet clover (Melilotus officinalis). This plant is readily infected by a variety of mycorrhizal fungi and becomes infected early in its development, often as seedlings. (See, Rogers R. D and Williams S. E., Soil Biol. Biochem., 18:371-376, 1986; Stahl P. D. and Williams S. E, 1986. Ibid.; and White J. A., Munn L. C. and Williams S. E., Soil Sci. Soc. Am. J., 53:86-90, 1989).

A known AM fungal inoculum was obtained from The International Culture Collection of (Vesicular) Arbuscular Mycorrhizae (invam.wvu.edu, Director Matt Kasson) maintained at the University of West Virginia in Morgantown, WV, US. A mixed culture of four AM fungal species was ordered. The mixture contained 250 ml of soil inoculum of each species. The total weight the entire mixed sample was 1345 grams and thus a bulk density of the sample of 1.345 g/ml. The material received contained the following species: Claroideoglomus etunicatum., Accession number AZ 201C (initially described by Becker W. N. and Gerdemann J. W., Mycotaxon, 6:29, 1977, as Glomus etunicatum.), spores were orange to red-brown, globose, subglobose; 60-160 μm diameter; mean 129 μm (n=120); Rhizophagus clarus, Accession number AZ 151D (initially described by Schenck, N. Mycologia, 71:182, 1979, as Glomus clarum.), spores are from white to yellow brown with many pale yellow to pale yellow brown, 100 to 260 μm diameter, mean 182 μm (n=120); Rhizophagus intraradices, Accession number AZ 123 (initially described by Schenck, N. Mycologia, 74:78, 1982, as Glomus intraradices), spores were white, pale cream, to yellow, brown, sometimes with a green hint, globose, subglobose, irregular. 40 to 140 μm diameter, mean 93.3 (n=170); and Septoglomus deserticola, Accession number CA 113 (initially described by Trappe J. Bluss and Menge J., 1984, Mycotaxon, 20:123, 1984, as Glomus deserticola), spores are orange-brown to dark red brown, most are reddish brown, globose to subglobose, sometimes irregular, 60 to 140 μm diameter.

The INVAM isolates at UWV were maintained on a 2 to 1 mixture of sand to soil. This mixture was steamed before use. The sand used was a fine silica sand (#4). The soil was from the UWV farm and had never been fully analyzed. It was described as a sandy loam with a pH of 6.2.

Inoculum was air dried prior to being received. It was maintained at this moisture level and stored at 1° C. until used, as recommended by INVAM. Before use in this example, the inoculum was passed through a 4 mm sieve and roots and aggregates that did not pass the sieve were crushed or removed.

To support the hypothesis that AM fungi can live free of living plants requires that AM fungi secure carbon from other sources in their soil habitat. Energy for metabolism could come from carbon in the soil habitat, but examples above suggest it comes from a separate source. Consequently, it was desired to use a native soil that was naturally high in organic matter but also one of near neutral pH and of a loamy texture. Several candidate soils were examined. The soil selected for this study was collected from a parcel of land maintained as grazing land for wildlife and a few livestock. The land had never been plowed and was occupied by native shrubs, forbs, and grasses. The pH of the soil was measured on site as 7.3 (2:1, distilled water to soil), soil color was dark, suggesting the organic matter content was at least 2% and perhaps as much as 4%. Classification of the soil was determined from the Albany County Soil Survey. (See, Reckner R.. Ibid. 1997, p. 540, map 68). The soil was determined to be either the Morset soil or the Lymanson loam. Both classify to the same taxonomic name: fine-loamy, mixed Argic Cryoborolls. In this report the soil will be referenced as the ML (Morset-Lymanson) soil.

The soil was collected in September. The site was dominated by the shrub bitterbrush (*Purshia tridentata*). Soil was collected from between the shrubs to a depth maximum of 15 cm. The soil was passed through a box sieve with 1.25 cm openings to remove coarse fragments and large pieces of organic debris. Just over 17 liters of soil were collected.

The present example was designed as a pot experiment where each pot was a treatment, the treatments being untreated controls, units treated with phosphate, and units treated with phosphite. All pots were a mixture of steamed ML soil, sand, and inoculum. Control units (pots) received no other treatment. Phosphate pots were treated with $K_2HPO_4$. Phosphite pots were treated with an equivalent molarity (concentration) of P as $K_2HPO_3$.

Half of the pots (a control, phosphate, and phosphite treatments) were planted with yellow sweet clover seed. The other half of the pots (also a control, phosphate, and phosphite treatment) were not planted with any plants.

The soil was steamed (described in more detail below) to deactivate some of the native microorganisms prior to the start of the study as well as deactivate all plant materials including roots and seeds. It is well recognized that steaming of soil under standard conditions will deactivate some fungi, likely some micro-arthropods and other soil microbiota. Many soil biota are not killed. Certainly, soil bacteria and actinomycetes remain largely unaffected. Most important, steaming of soil does not modify substantially the physical or chemical properties of the soil and does not impact the growth of added mycorrhizal fungi. (See, Abbott L. K. and Robson A. D., "The Effect of VA Mycorrhizae on Plant Growth," In: Powell C. L. and Bagyaraj J. "VA Mycorrhizae," CRC Press, Boca Raton, FL, 1984, pp. 113-130).

Steaming was accomplished using a steam pressure chamber. The ML soil material was placed in round, aluminum pans (22 cm diameter by 3.2 cm depth). Each pan held a soil volume of about 1.6 liters of soil. Four pans of soil provided the needed volume of soil. The four pans were stacked in the pressure chamber, with a separator in the chamber bottom, and wooden slats separating (1.5 cm) each pan from the others. The pressure chamber was activated and brought to pressure of 10.34 kPa and held at that pressure for 45 minutes. Once the steaming cycle was completed, the chamber was allowed to cool to ambient temperature.

Steaming is a standard technique for partially sterilizing soil to depress microbial activity and deactivate all plant seeds and other plant parts, e.g., roots, stems, etc. (Fennimore S. A., "Steaming and Other Management Practices of Pre-plant Weed Control in Nurseries," University of California, Division of Agriculture and Natural Resources, obtained from ucnfanews.ucanr.edu, October, 2021). Accordingly, seeds are deactivated in soil at a temperature of 82.2° C. if that temperature can be maintained for 30 minutes.

Autoclaving (121° C., 13.75 kPa, for a minimum of 20 minutes) is noted widely as a way to completely sterilize soil. However, complete sterilization will modify the nutritional status of soils and often releases toxins into the soil. (See, Abbott, L. K. and Robson A. D., Ibid. 1984). The method described below does not completely sterilize the soil, but it is more aggressive than partial sterilization which is a result of standard steaming.

The average atmospheric pressure at the experiment site was 78.930 kPa. Addition of the 10.34 kPa imposed by the pressure chamber brought this to 89.270 kPa (Lide 1999, Ibid., p. 14-17). At this pressure, the boiling point of water is about 96° C., which is sufficient to kill all plant seed and other parts as well many of the other life forms in the soil. (Lide 1998-1999, Ibid., p. 6-10).

The sand used in this study was a washed quartz sand of 2.00 mm maximum grain diameter. This material is provided in 22.6 kg bags and widely and commercially available, e.g., QUIKRETE® premium play sand No. 1113-51.

The volume of each pot that would accommodate the soil material was 3,150 ml (diameter of 17.78 cm and depth of 12.7 cm). However, a layer of inert stones (water polished granite) were spread in the bottom of each pot to provide drainage of water out of the pot. A single layer of brown, inert paper was used to cover the stones to keep the added soil from penetrating into the drainage layer. The volume of soil material was then placed on top of stones and paper was measured at 2,325 ml. This was the volume of soil material prepared for each pot. The weight of soil material was estimated at 3,022.5 grams (the product of 1.3 g/ml and 2,325 ml). The weight was measured gravimetrically at 3,022.5 g. This constituted 1,000 ml of soil and 1,200 ml of sand and 125 ml of inoculum per pot (or about 43% soil, 51.6% sand and 5.4% inoculum.

Phosphate and phosphite were added to the soil materials such that the phosphorus in each would constitute 80 mg per kg of soil (Table 6). This is more than was added to the field experimental plots described in Example 3. However, the results of that experiment (Example 4) did show a response of the AM fungi to phosphite. In Example 4, phosphorous either as phosphate or phosphite, was added at 61.53 ppm. In Example 4, there was no apparent inhibition of infection or spore production by addition of phosphorus. The level of P was raised to 80 mg per kg in this example to accentuate the impact of added P on the AM fungi. Each pot described in Table 6 contained 3.022.5 g of soil material (soil plus sand and inoculum).

In Table 6, the pot volume was 2,325 ml and weighed at 3,022.5 g. However, the P added was scaled to a weight of 3,055 g for each pot to allow enough extra soil material for chemical analysis at the start of the study. The phosphorous acid was added as the dipotassium salt and was converted to the salt by dissolving the acid in 400 ml of distilled water and adding 1.771 grams of KOH (15.78 mmoles) to convert the phosphorous acid to dipotassium phosphite according to the chemical equation: $H_3PO_3 + 2KOH \rightarrow K_2HPO_3 + 2H_2O$.

TABLE 6

| Pot Treatment | Added P Kg/Ha | Added P (µg/g, or ppm) |
| --- | --- | --- |
| Control | 0 | 0 |
| $K_2HPO_4$ | 160 | 80 |
| $H_3PO_3$ | 160 | 80 |

The various treatment substrates, i.e., soil, sand, and inoculum, were mixed in batches. The control batch was established and mixed for the control treatments. Likewise, the phosphate and phosphite batches were mixed, respectively, for all phosphate and phosphite treatments. The treatments salts ($K_2HPO_4$ and $K_2HPO_3$) were added as 400 ml aqueous solution (chemical in distilled water to 400 ml). Control treatments were performed in the same manner except 400 ml of distilled water only was added to each pot. Table 6 shows P additions to the phosphate and phosphite single pots.

The batches of soil materials were thoroughly mixed using a sterilized (ethanol and flaming) trowel. The mixing was performed by hand with each batch of soil material being mixed for 40 minutes in this manner. After mixing, the batches were noted as being too damp to effectively distribute in pots. The batches were then allowed to air dry for 48 hours. Afterwards, soils were distributed in pots with small samples retained for analysis. Pot soils were tamped slightly so that they filled the pots without large voids in the soil materials matrix.

The pots were placed on a raised platform with sides about a meter off the ground at the same location as that of the Example 3 and 4 plots (2,277 meters elevation and Lat/Long of 41.32° N and 105.67° W). One pot each of the control, phosphate, and phosphite samples were planted with yellow sweet clover seeds. The three planted pots were each scarred with a three-tined hand rake to a depth of 1 cm. Thirty seeds were planted in each pot, with approximately ten seeds distributed evenly along each of the three rows and the soil tamped down gently. The other control, phosphate and phosphite pots were left void of plants. Distilled water (200 ml) was distributed evenly over each of the pots—planted and unplanted.

Cultural conditions were divided into two phases (Table 7): an outdoor phase under natural sunlight and precipitation, with supplemental water, and an indoor, controlled phase under natural sunlight and supplemental light and water (Phases I and II, respectively). The experimental samples were moved into the controlled environment largely because of the onset of cold weather. Phase I began in mid-September and ran for a duration of 34 days. Phase I included replanting of the yellow sweet clover seed on day 16.

Phase II lasted from 21 October and ran for a duration of 34 days (Table 7). During this phase plants were in a controlled environment. Sunlight averaged 8 hours per day and supplemental light was applied for about 12 hours. Sunlight came largely from the SSW (200°) and the WNW (300°). Supplemental lighting was a height of 28 cm above the surface of the soil material in the pots. The LED lights provided full spectrum at luminous flux 24,000 lm. Temperature during Phase II was 16 to 17° C. From October 21 through November 22 pots and plants received daylight and supplemental light. On the 22nd, supplemental light stopped, and plants moved to an environment of temperatures 7° C. to 10° C. The study was ended November 24, on which date the plants and soil were sampled. During phase II pots received 100 ml $H_2Od$ on every third day.

TABLE 7

| PHASE I | | | Temperature, ° C.[2] | | Ppt.[3] |
|---|---|---|---|---|---|
| | | | High | Low | |
| Month | Date | | Day or Mo | Day or Mo | cm |
| Sept | 17 | 400 ml $H_2Od$[1] per pot. Pots outside. | 24.4 | 2.8 | |
| | 19 | YBSC[4] planted. 200 ml H2Od per pot | 25 | 7.8 | |
| | 20 | 50 ml $H_2Od$ to each pot as mist | 22.2 | 6.1 | |
| | 21, 22 | 50 ml $H_2Od$ to each pot as mist twice | 25 | 3.9 | |
| | 23 | $H_2Od$ 100 ml and 200 ml, respectively | | | |
| | 25 | 100 ml $H_2Od$ per pot | 24.4 | 3.9 | |
| | | | | | 0.28 |
| | 27 | Pots moved inside. Low of-4 predicted | 11.7 | −3.3 | snow |
| | 28 | Inside temp varied from 10 to 14° C. | 13.3 | −7.2 | |
| | 29 | Pots returned outside. 200 ml $H_2Od$ per pot | 23 | −0.6 | |
| | 30 | Poor germination noted. Damaging wind. | 20 | 0 | |
| | | | | | Total |
| | Average: Sept 17 to Sept 30, all dates inclusive. | | 22.1 | 3.1 | 0.28 |
| Oct | 1 | New seed secured. Imbibition started | 17.2 | −2.8 | |
| | 2, 5 | 50 ml $H_2O$ added twice as mist | | | |
| | 6 | New YBSC seed planted | 23.3 | 2.2 | |
| | 7, 10, 13 | 100 ml $H_2Od$ per pot each day | | | |
| | 15, 18 | 100 ml $H_2Od$ per pot each day | | | |
| | 21 | Pots permanently moved inside to controlled environment. | | | |
| | Average: Oct 1 to 21, all dates inclusive. | | 17.8 | 1.1 | Total 0 |

| PHASE II | During this phase plants were in a controlled environment. Sunlight averaged of 8 hours a day and supplemental light 12 hours. Sunlight came largely from the SSW (200°) and the WNW (300°). Supplemental lighting was a height of 28 cm above the surface of the soil material in the pots. The LED lights provided full spectrum at luminous flux 24,000 lumen. Temperature during phase II was 16 to 17° C. From October 21 through November 22 pots and plants received daylight and supplemental light. On the 22nd, supplemental light stopped, and plants moved to an environment of temperatures 7 to 10° C. The study was ended November 24, plants and soil sampled. During phase II pots received 100 ml $H_2Od$ on every third day. |
|---|---|

Notes:

[1]$H_2Od$: Distilled water.

[2]Temperatures recorded at the NOAA weather station at the Laramie Regional Airport located 11 km west of the test site at 2,216.5 m elevation (datum mean sea level) at Lat/Long of 41.32° N and 105.67° W.

[3]Precipitation recorded at study site 2,277 m elevation, Lat/Long of 41.32° N, 105.54° W.

[4]YBSC: Yellow sweet clover (*Melilotus officinalis*), also called yellow blossom sweet clover.

As the experiment was dismantled, soil moisture of pot soils was determined, total weight of soil in each pot was recorded, soils were air dried (19° C.), 400 gram subsamples were taken for chemical analysis, root samples were extracted for staining, above ground plant parts were removed, and 100 gram subsamples were taken for determination of spore numbers.

Soil analysis (Table 8) were performed using standard soil methodologies: extractable (plant available) phosphate and total phosphorus (Olsen, S. R. and L. E Sommers, 1982, Ibid., pp. 403-430); nitrate, ammonium, and total nitrogen (Bremner, J. M. and Mulvaney C. S., Ibid., pp. 595-624); organic carbon (Skjemstad, J. O. and Baldock J. A., 2008, Chapter 21, "Total and Organic Carbon," In: Carter M. R. and Gregorich E. G., "Soil Sampling and Method of Analysis," CRC Press, Boca Raton, FL, 2007, pp. 225-237), and pH and Electrical conductivity (Gavlak, R., D. Horneck R. D., and Miller R. O., 2005, Ibid.). SAR (the Sodium Adsorption Ratio) was calculated for the several treatments prior to the start of the study. SAR is based on the cations in the saturation extract of the soil. The cations Ca, Mg, and Na were determined and expressed as millimoles per liter (mmoles per L). The SAR is calculated as follows:

$$SAR=[Na]/[([Mg]+[Ca])/2]^{0.5}$$

For Table 8A and 8B (below): Soil analysis were from the Nov. 27, 2020, samples from the pot study. TKN: Total Kjeldahl Nitrogen, TOC: Total Organic Carbon, pH made on 2:1 $H_2Od$ (distilled water) to soil, EC: electrical conductivity taken on 2:1 $H_2Od$ to soil, (H+): hydrogen ion activity, dS: deci-Siemans, SD: Standard Deviation. Table 8A provides analysis of the Sep. 17, 2020, pot study samples. The ML soil prior to steaming and dilution with sand and inoculum was 52 ppm Ext P, 580 mg/Kg Total P, 3.8% organic C, pH of 5.9, EC of 0.35 dS/m, SAR of 0.112, and K of 30.7 ppm. After steaming, ML soil was still pH of 5.9, but EC increased to 0.78. Start conditions (Sep. 17, 2020) from analyses of the control soil: 2.8, 4.0, and 100 ppm, nitrate N, ammonium N, and TKN, respectively. All beginning treatments had similar organic C of 0.8 (0.1 SD) %, and pH of 7.7 (0.2 SD). EC increased from the control to the treatments reflecting the addition of the phosphorus as the K salts. This is reflected in the increase in the SAR and confirmed with the K analysis. TKN: Total Kjeldahl Nitrogen. TOC: Total Organic Carbon. pH made on 2:1 H2Od (distilled water) to soil, EC: electrical conductivity taken on 2:1 H2Od to soil, (H+): hydrogen ion activity, dS: deci Siemans, SD: Standard Deviation.

Table 8B provides analysis of the Nov. 27, 2020, pot study samples.

TABLE 8A

| Sample ID | Extracted P ppm | Total P mg/kg | Organic Carbon % | pH -log (H+) | EC dS/m | SAR | K ppm |
|---|---|---|---|---|---|---|---|
| Control (C) | 21 | 420 | 0.7 | 7.9 | 1.04 | 0.597 | 39.4 |
| Phosphate ($PO_4$) | 92 | 420 | 0.8 | 7.5 | 1.44 | 0.825 | 131.5 |
| Phosphite ($PO_3$) | 121 | 470 | 0.9 | 7.7 | 1.48 | 0.631 | 149.9 |

TABLE 8B

| Sample ID | Extracted P ppm | Total P mg/kg | pH -log (H+) | EC dS/m |
|---|---|---|---|---|
| Control, no plants[1] | 19 | 370 | 7.7 | 0.85 |
| ($PO_4$) no plants[1] | 100 | 410 | 7.6 | 1.27 |
| ($PO_3$) no plants[1] | 96 | 470 | 7.7 | 1.12 |
| Control, planted[2] | 19 | 350 | 7.7 | 0.81 |
| ($PO_4$) planted[2] | 98 | 410 | 7.6 | 1.24 |
| ($PO_3$) planted[2] | 97 | 470 | 7.7 | 1.09 |

[1] Pots contained no plants of any kind.
[2] Pots planted with yellow sweet clover (*Melilotis officinalis*).

An SAR above 13 is considered to be a sodic soil. The SARs in this example were all less than unity and present no sodium hazard (Soil Science Society of America, 2001, Glossary of Soil Science Terms, On-line, soils.org/publications/soils-glossary/#, accessed October of 2021). In addition, the low electrical conductivities (ECs) indicate that salinity is low enough to have almost negligible effects on plants. (See, Miller, J. J. and Curtin D., 2008, Chapter 15, "Electrical conductivity and soluble ions," In: Carter and Gregorich, "Soil Sampling and Methods of Analysis," CRC Press, Boca Raton, FL, 2008, pp. 161-171).

The ML soil prior to steaming was 52 ppm Ext P, 580 mg/Kg Total P, 3.8% organic C, pH of 5.9, EC of 0.35 dS/m SAR of 0.112, and K of 30.7 ppm. After steaming, the ML soil was still pH of 5.9, but EC increased to 0.78. Start conditions (Sep. 17, 2020) shown in analyses of the control soil: 2.8, 4.0, and 100 ppm nitrate N, ammonium N and TKN, respectively. All of the beginning treatments had similar organic C of 0.8 (0.1 SD) %, and pH of 7.7 (0.2). EC increased from the control to the treatments reflecting the addition of the phosphorus as their K salts. This is reflected in the increase in the SAR and confirmed with the K analysis.

The average organic carbon in the soil materials was 0.8% (0.15 SD), pH 7.7 (0.2), and EC 1.32 dS/m (0.24 dS/m). Although the average extractable P in the phosphate ($PO_4$) treatments was 96.7 (4.2) ppm as compared to the average extractable P in the phosphite (P03) treatments 105 (14.2) ppm, these mean values were not statistically different (alpha of 0.188). However, the difference between extractable P from the phosphate treatments mean and the control mean were highly significant (alpha of $3.28 \times 10^{-6}$) as was the difference between extractable P from the phosphite treatment mean and the control mean (alpha of $2.23 \times 10^{-4}$).

Roots from the planted pots were removed and processed for microscopic viewing according to Phillips, J. M. and Hayman, D. S. 1970. (Improved procedures for clearing roots and staining parasitic and vesicular-arbuscular mycorrhizal fungi for rapid assessment of infection. Trans. Brit. Mycological Soc. 55:158-160) except that lactic acid glycerol was used with trypan blue. The analysis of the roots proceeding generally according to the following protocol:

A) Remove roots from FAA Solutions. Cut into 1 cm lengths. Place in test tube, push roots to the bottom of the test tube.
B) Cover roots with 10% KOH (10 grams of reagent grade KOH in enough distilled water to 100 ml). Let stand overnight or for about 10 hours.
C) Incubate roots at 90° C. for one hour in a water bath (container with water and test tubes with roots over a heat source).
D) Rinse in tap water.
E) Rinse five minutes in 0.1 N HCl (3.65 gram equivalents of HCl in 1000 ml total volume with distilled water).

F) Rinse in tap water.

G) Incubate roots at 90° C. one hour (In water bath) in trypan blue lactic acid glycerol (distilled water, 100 ml; lactic acid (reagent grade 85 to 88%) 100 ml; glycerin (reagent grade 85% also listed as glycerol), 200 ml; trypan blue, 0.1 grams (60% dye content).

H) Rinse in tap water.

I) Place in clear lactic acid glycerol (same formulation as above except without the trypan blue) if de-staining is necessary. Samples can be incubated at 90° C. one hour (In water bath) or left at room temperature for at least 72 hours or longer.

J) Mount on standard glass slide (2.5 cm by 7.6 cm) in lactic acid glycerol. Cover slip (2.3 cm by 4.8 cm) used.

Mounting of roots and observation of roots was performed initially at a cursory level using a dissecting microscope (United Scope, LLC, Irvine, CA, 3.5× to 90× stereomicroscope). Comprehensive microscopic analysis was conducted using a compound, light microscope (Leica Microsystems, Buffalo Grove, IL, US; DMLB Research Microscope: bright field and DIC applications. With 10×/22 mm eyepieces, N Plan 10×, 20× and 40× objectives and mechanical stage with slide holder).

Spore extraction and quantification, data presented in Table 9, was performed according to the following general protocol:

A) Weigh 5 g of air dried soil into a 20 ml centrifuge tube. For a complete sample replicate this four times.

B) Fill each tube with water to ~1.5 cm of the top. Stir to suspend organic matter and other light debris. Let all tubes stand for 10 minutes.

C) Centrifuge at 2000 rpm (475.2×g) for 10 minutes.

D) Pour off and discard supernatant while stirring surface and rotating tube.

E) If much organic matter and other light material remains, repeat steps 2 through 4.

F) Add sucrose/sodium hexametaphosphate solution (2 molar sucrose containing 2% hexametaphosphate: 684.6 g of sucrose and 20 g of sodium hexametaphosphate in one liter of solution using distilled water) to centrifuge tubes to ~1.5 cm of top. Stir vigorously for three minutes to suspend. Let tubes stand 10 minutes.

G) Centrifuge for 10 minutes at 2000 rpm (475.2×g).

H) Decant and save supernatant. Discard solids in tube bottoms.

I) Add collected supernatants from the four tubes to a separatory funnel. Let stand for 10 minutes.

J) Set funnel to drip (one drop at a time). Discard liquid passing through funnel.

K) Wash materials sticking to the funnel wall into a petri dish using a minimum amount of water.

L) View and count spores under dissecting scope.

Viewing and counting spores was performed using the stereoscopic dissection microscope scope. Calculations of the number of spores per 100 g of soil was accomplished according to the procedures of Watson, 1987. Ibid. (See also, Allen M. F., Moore T. S. Jr, Christensen M., and Stanton N., 1979, *Mycologia*, 71:666-671). This procedure was modified in that the bottom of the petri dish was fitted with graph paper showing 1 $cm^2$ sectors. Ten sectors were randomly selected from the total 62.21 $cm^2$ area of the petri dish bottom. Spores were randomly distributed throughout the petri dish bottom using a narrow stream of water. Spores in each 1 $cm^2$ sector were counted and the ten sectors totaled. The sum was multiplied by 31.05 (6.21×5; to get the total number of spores in the petri dish. The total of the ten 1 $cm^2$ sectors was multiplied by 6.21, the factor to bring the spore estimate to the total for the entire petri dish; the spore number in the petri dish represent the total in 20 grams of soil. Needed is the number for 100 grams, the standard manner to report spore numbers and thus the total number of spores in the petri dish multiplied by 5 provides this estimate).

Table 9 describes the phosphorus treatments, Total P, pH, EC and AM spore density and infection rates of units in the pot study. INVAM inoculum was the living cultures from the International Culture Collection of (Vesicular) Arbuscular Mycorrhizal fungi. This was a mixture of four species (see text) and is the characterization of the undiluted inoculum prior to the start of incubation. The three treatments show characteristics of the soil materials at the start of incubation (Sep. 17, 2020) at t=0 days. The six treatments show the characteristics of the soil material as well as spore counts and infection levels at the end of incubation (Nov. 22, 2020) at t=66 days.

TABLE 9

| Sample ID | Treatment P ppm | Extracted P-Control ppm | Extracted P ppm | pH – log ($H^+$) | EC dS/m | AM Fungal Spores per 100 g soil | AM Infection level, %[1] |
|---|---|---|---|---|---|---|---|
| INVAM Inoculum[2] | | | | 6.2 | | 7,923 | |
| START OF STUDY AT 0 DAYS. | | | | | | | |
| Control | 0 | 0 | 21 | 7.9 | 1.04 | 408[\3] | |
| Phosphate | 80 | 71 | 92 | 7.5 | 1.44 | 408[\3] | |
| Phosphite | 80 | 100 | 121 | 7.7 | 1.48 | 408[\3] | |
| END OF STUDY AT 66 DAYS | | | | | | | |
| Control no plants[4] | 0 | 0 | 19 | 7.7 | 0.85 | 2,299 | |
| Phosphate no plants[4] | 80 | 81 | 100 | 7.6 | 1.27 | 5,220 | |
| Phosphite no plants[4] | 80 | 77 | 96 | 7.7 | 1.12 | 7,301 | |

TABLE 9-continued

| Sample ID | Treatment P ppm | Extracted P-Control ppm | Extracted P ppm | pH – log (H+) | EC dS/m | AM Fungal Spores per 100 g soil | AM Infection level, %[1] |
|---|---|---|---|---|---|---|---|
| Control, YBSC plants[5] | 0 | 0 | 19 | 7.7 | 0.81 | 8,389 | 82.5 |
| phosphate, YBSC plants[5] | 80 | 79 | 98 | 7.6 | 1.24 | 7,146 | 47.5 |
| Phosphite, YBSC plants[5] | 80 | 78 | 97 | 7.7 | 1.09 | 4,598 | 35 |

Notes:
[1] Number of infected 1.1 mm root segments per 80 examined, %.
[2] The inoculum had a pH of 6.2, but other characteristics of the inoculum soil material was unavailable from INVAM.
[3] Each pot weighed 3,022.5 grams. Of this each pot had 154.8 grams of whole inoculum. Thus, each pot was 5.122% inoculum. Each pot therefore started with a total number of spores of 12,265, or about 408 spores per 100 grams of soil, from the IMVAM inoculum.
[4] No plants of any kind. Pots were checked daily to be sure there were no volunteers.
[5] Planted with yellow sweet clover (YBSC, *Melilotus officinalis*). About 90 seeds were planted per pot and thinned to 15 per pots within two days of germination.

As reported in Table 9, all treatments showed increases in spore populations in the 66 days of incubation. The spore population level at the start of the incubation in the various treatments was 408 spores per 100 grams of soil. At the end of the incubation period where treatments included planting with yellow sweet clover, spore populations had increased to 8,389 in the control, an increase of over 20 fold (2,056%) from the start of the study. In the planted phosphate treatment, the increase was nearly as much, 1,751%, whereas the change in spore population in the phosphite treatment was 1,127%.

That the spore population in the planted control was so high is consistent with most studies of AM fungi. The plants in this case provide expected nutrition to the fungi which is confirmed by the infection rate in the plants. Spore populations in the planted phosphate treatment are also high, but may be exhibiting slower development. Many researchers report inhibition of AM fungi by high levels of P. This is confirmed given the infection of plants in this treatment is also low. That the spore population is lowest in the phosphite treatment may reflect inhibition of the plant by phosphite which may have feedback on the fungus either as lack of available metabolites from the plant, inhibition of the AM fungi by the phosphite, or both. That the infection level in this treatment is so low indicates the symbiosis between plant and fungus is compromised by the presence of phosphite.

The spore population development in the treatments where plants were absent showed increases. The unplanted control had the lowest increase of any treatment, planted, or not planted. The spore population increased by only by 563%. The unplanted phosphate treatment increased by 1,279%, but the unplanted phosphite treatment increase at time 66 days over the levels at time 0 was 1,789%.

The interpretation of these results is that despite the treatment there was some considerable increase in spore numbers from the inoculum. It is possible that some spores were still present and active in the ML soil. That is, it is possible that the steaming process did not deactivate all spores and thus the counts of spores (AM Fungal spores per 100 g soil, Table 9) represents not only the spores from the inoculum but also spores from the native mycorrhizal populations from the ML soil. There were undoubtedly spores of AM fungi present in the native ML soil that had not been steamed. Grasses and shrubs were present on the site including the shrub bitterbrush (*Purshia tridentata*). Bitterbrush is known to be a host for AM fungi. (See, Williams, S. E., *Bot. Gaz.*, 140(Suppl.):113-119, 1979). However even if the spore count included enough spores from the ML soil to raise the level of that observed in the unplanted control soil (2,299 spores per 100 g of soil, Table 9), this certainly does not explain increases in spore populations of all the other treatments, especially in the unplanted treatments.

The increase in the spore numbers in the planted control is, according to observations and published accounts, expected. The level of extractable P in this treatment was low and plant roots were prevalent throughout the treatment container by the end of the incubation and plant growth period (66 days). However, noted here is that of the spore population counted, the majority of spores in this treatment were small and immature (4,257 per 100 g of soil). This was true also for the planted phosphate treatment (3,604 small, immature spores per 100 g soil). Only the planted phosphite treatment showed relatively few small immature spores (217 per 100 g soil) and showed that a majority of the spore population was of mature, brownish reddish spores (3,480 per 100 g soil). The planted control and planted phosphate treatment had mature brownish reddish spore populations of 3,387 and 2,827 per 100 g soil, respectively. The interpretation is that in both the planted control and planted phosphate treatments, the preponderance of immature spores over mature spores in these treatment soils suggests the AM fungi were still highly active and probably with more incubation and plant growth time would have produced more mature spores. The absence of immature spores in the phosphite treatment and the relative abundance of mature spores is because the fungi in this treatment being less active and likely had reached a maximum spore population.

Some of the interpretation of spore populations in the planted treatments also apply, with caveats, to the unplanted treatments. The unplanted control treatment had very few small, immature spores (435 per 100 g soil), and relatively high brownish reddish mature spores (1,119 per 100 g soil). The implication from these data is that the AM fungi in this treatment were not in an expanding growth mode. The phosphate treatment however, had high levels of small, white immature spores (2,548 per 100 g soil) as well as high levels of mature brownish reddish spores (2,237 per 100 g soil). This suggests that the AM fungi in this treatment were fairly active. It is likely this population has finalized expanding its population. Alternatively, the population may be maturing and more mature spores were forthcoming.

The unplanted phosphite spore population dynamics suggests an alternative response. In these samples the population of brownish reddish mature spores was high (4,287 per 100 g soil) and the small immature spore population was lower (1,585 per 100 g soil). Also, there was a population of light colored to white spores that developed in this unplanted treatment that did not develop to the same extent as in the other treatments. The light to white population was 1,429 spores per 100 g soil, and was more than twice the population of this spore type than observed in any other treatment. These data suggest that the AM fungi in this treatment were very active even at 66 days past the start of the experiment. Mature spores were being produced in two categories (likely two species) as the immature spores matured.

From the description of the species spores from the INVAM collection, it is conjectured that the brownish reddish spores are *Septoglomus deserticola*, and white spores are of the species *Rhizophagus intraradices*. It is likely that the *S. deserticola* has some color overlap with *Claroideoglomus etunicatum*. The *C. etunicatum* does have some brownish to reddish colors. Likewise, *R. intraradices* has some color overlap with *Rhizophagus clarus*, both being relatively light colored. The point is, however, that in this treatment, several morphology and color types of AM fungi are increasing well above any other treatment, planted or unplanted, in this study.

The observation that there can be an increase in spore numbers in the absence of host plants has never before been reported.

Without wishing to be bound by theory, an interpretation of the evidence presented herein is that AM fungi are able to either directly or indirectly utilize the energy available from the oxidation of phosphite to phosphate. Carbon is obtained from most likely soil organic matter. This obviates the presence of a plants susceptible to AM fungal infection for the growth and reproduction of AM fungi. Such a conclusion explains the high production of spores in the unplanted phosphite treatment.

The breadth and scope of the present disclosure should not be limited by any of the above-described exemplary embodiments, but should be defined only in accordance with the following claims and their equivalents. That is, the above examples are included to demonstrate various exemplary embodiments of the described methods and systems. It will be appreciated by those of skill in the art that the techniques disclosed in the examples represent techniques discovered by the inventor to function well in the practice of the described methods and systems, and thus can be considered to constitute optional or exemplary modes for its practice. However, those of skill in the art will, in light of the present disclosure, appreciate that many changes can be made in these specific embodiments that are disclosed and still obtain a like or similar result without departing from the spirit and scope of the described methods and systems.

What is claimed is:

1. A method of growing and/or improving the growth of plants obligatively or facultatively dependent on arbuscular mycorrhizae fungi (AMF) by growing the plants in soil comprising an active population of AMF spores, wherein the soil is produced by a process, which comprises:
    a) providing a first soil;
    b) killing living plant material in the first soil by applying one or more plant killing procedures to the first soil;
    c) providing an active culture comprising the population of AMF spores in a first location;
    d) adding phosphorous as phosphate and/or phosphite to the first soil;
    e) amending the first soil with the population of active AMF the spores to yield an AMF-amended soil that comprises about 2 to about 10 active AMF spores per gram of the first soil;
    f) incubating the AMF-amended soil for several days to several months under conditions conducive to AMF spore propagation, wherein the conditions conducive to AMF spore propagation comprise:
    adding water to the soil,
    and optionally
    exposing the soil to light, and then
    g) planting one or more of the plants in the AMF-amended soil,
    wherein the active AMF spores propagate during incubation thereby producing AMF-amended soil comprising about three-fold more active AMF spores per gram of the soil than provided in step e),
    wherein during steps a) through f), no living plant material is amended to the first soil.

2. The method of claim 1, further comprising:
    h) transporting the AMF-amended soil to a second location which optionally comprises a second soil, and
    i) amending the second soil with the AMF-amended soil co.

3. The method of claim 1, wherein the first soil comprises a total organic carbon (TOC) content of greater than 0.5 wt % and less than 4.0 wt % as determined by a dry combustion method or a dichromate redox method, and wherein the total organic carbon comprises dead and decaying remains of plants, animals, microorganisms, and associated metabolic constituents thereof.

4. The method of claim 1, wherein the phosphorous and/or phosphite in step d) comprises: phosphate anion $PO_4^{-3}$ and/or phosphite anion $PO_3^{-3}$ and
    wherein the phosphorous is present in the first soil at a final concentration of at least about 61 ppm.

5. The method of claim 1, wherein the light is full spectrum luminous flux of at least 24,000 lumens, and/or wherein the first soil is exposed to light for a period of 8 to 20 hours of each 24 hour period after inoculation.

6. The method of claim 1, wherein adding water to the first soil comprises:
    first adding an initial 400 mL water per 3,055 g of the first soil, and then 100 mL per 3,055 g of the first soil every third day after inoculation, and/or
    adding an initial 400 mL water per 3,055 g of the first soil, and then adding 100 mL water per 3,055 g of the first soil every third day.

7. The method of claim 1, further comprising the steps of:
    air-drying the first soil after step b) and prior to step c), and/or
    packaging the first soil after step e) into containers for transport.

8. A method of growing arbuscular mycorrhizae fungi (AMF), which comprises:
    i) providing soil in which the plant is to be grown,
    ii) killing any pre-existing live plant material in the soil,
    iii) adding phosphorous as phosphate and/or phosphite to the soil,
    iv) amending the soil with active AMF spores to the soil such that the AMF-amended soil comprises about 2 to about 10 active AMF spores per gram of the soil, v) adding water to the soil, vi) incubating the AMF-amended soil until the soil comprises at least about 3-fold more active AMF spores per gram of the soil than active culture added, and vii) planting an AMF-obligate mycotrophic or AMF-facultative mycotrophic plant or a seed thereof into the AMF-amended soil, wherein during steps i) through vi), no living plant material is amended to the soil.

9. The method of claim 8, wherein killing pre-existing live plant material in the soil comprises applying one or more of pressurized steam, UV radiation, and ethylene oxide to the soil, such that the soil comprises no detectable living plant material.

10. The method of claim 8, wherein the soil is located on a farm, a reclamation site, a greenhouse, a plantation, or a grove.

11. The method of claim 8, wherein the pre-existing live plant material in step ii) comprises: living plants or reproductive structures thereof from a prior planting in the soil, and/or weeds and/or native plant species or reproductive structures thereof existing in the soil prior to the method.

12. The method of claim 8, wherein the phosphate and/or phosphite in step iii) comprises one or more of: phosphate anion $PO_4^{-3}$ and/or phosphite anion $PO_3^{-3}$ and wherein the phosphorous is present in the soil at a final concentration of at least about 61 ppm.

13. The method of claim 8, wherein adding water to the soil comprises:

adding an initial amount of water upon inoculation and then adding water every third day after inoculating, or adding an initial 400 mL water per 3,055 g of soil, and then adding 100 mL water per 3,055 g of soil every third day.

14. The method of claim 8, wherein the light is full spectrum luminous flux of at least 24,000 lumens, and/or wherein the soil is exposed to light for a period of 8 to 20 hours of each 24 hour period after inoculation.

15. The method of claim 8, wherein the soil comprises a total organic carbon (TOC) content of greater than 0.5 wt % and less than 4.0 wt % as determined by a dry combustion method or a dichromate redox method, and wherein the total organic carbon comprises dead and decaying remains of plants, animals, microorganisms, and associated metabolic constituents thereof.

16. The method of claim 8, wherein the plant or the seed thereof is an obligate mycotroph or a facultative mycotroph.

\* \* \* \* \*